(12) United States Patent
Dennis et al.

(10) Patent No.: US 8,292,862 B2
(45) Date of Patent: Oct. 23, 2012

(54) DYNAMIC FITTING BODY ADHERING ABSORBENT ARTICLE

(75) Inventors: Melissa Jean Dennis, Appleton, WI (US); Russell Frederick Ross, Atlanta, GA (US); Luke Hagan, Providence, RI (US); Thomas Andrew Lutzow, Providence, RI (US); Gerhard Andrew Foelsche, Rehoboth, MA (US); Aidan J. Petrie, Jamestown, RI (US); Alan Schinazi, Providence, RI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 618 days.

(21) Appl. No.: 12/507,703

(22) Filed: Jul. 22, 2009

(65) Prior Publication Data

US 2010/0057034 A1    Mar. 4, 2010

Related U.S. Application Data

(63) Continuation-in-part of application No. 12/364,486, filed on Feb. 2, 2009, which is a continuation-in-part of application No. 11/890,093, filed on Aug. 3, 2007, and a continuation-in-part of application No. 12/005,793, filed on Dec. 28, 2007, now Pat. No. 7,947,027.

(51) Int. Cl.
 *A61F 13/15* (2006.01)
 *A61F 13/20* (2006.01)
(52) U.S. Cl. .................... 604/385.03; 604/387
(58) Field of Classification Search ............ 604/385.17, 604/385.22, 378, 385.03, 387
See application file for complete search history.

(56) References Cited

U.S. PATENT DOCUMENTS

| | | | |
|---|---|---|---|
| 2,842,897 A | 7/1958 | Finn |
| 3,288,346 A | 11/1966 | Peppler |
| 3,338,992 A | 8/1967 | Kinney |
| 3,341,394 A | 9/1967 | Kinney |
| 3,502,538 A | 3/1970 | Petersen |
| 3,502,763 A | 3/1970 | Hartmann |

(Continued)

FOREIGN PATENT DOCUMENTS

EP     0 638 303 B1    11/1997

(Continued)

OTHER PUBLICATIONS

Patent Cooperation Treaty Search Report from the International Search Authority, International Application No. PCT/IB2009/055744 dated Sep. 14, 2010.

(Continued)

*Primary Examiner* — Melanie Hand
(74) *Attorney, Agent, or Firm* — Randall W. Fieldhack

(57) ABSTRACT

A disposable personal care article comprises a shell having a unitary structure for disposition adjacent a wearer's vulva region, where the shell has a first side and a second side, the first side having a first area and a second area. The first area of the shell contacts to the wearer's skin and/or hair surrounding the vulva region. At least a portion of the first area comprises a body attachment means for adhering the shell directly to the skin and/or hair of the wearer. In addition, the shell has an anterior half and a posterior half where the posterior half exhibits a higher extension relative to the anterior half when a stretching force of 454 grams is applied. In some aspects, the article further includes an absorbent structure.

20 Claims, 16 Drawing Sheets

U.S. PATENT DOCUMENTS

| | | |
|---|---|---|
| 3,542,615 A | 11/1970 | Dobo et al. |
| 3,692,618 A | 9/1972 | Dorschner et al. |
| 3,802,817 A | 4/1974 | Matsuki et al. |
| 3,849,241 A | 11/1974 | Butin et al. |
| 3,963,029 A | 6/1976 | Brooks |
| 3,972,328 A | 8/1976 | Chen |
| 4,072,151 A | 2/1978 | Levine |
| 4,340,563 A | 7/1982 | Appel et al. |
| 4,488,928 A | 12/1984 | Ali Khan et al. |
| 4,505,976 A | 3/1985 | Doehnert et al. |
| 4,631,062 A | 12/1986 | Lassen et al. |
| 4,673,403 A | 6/1987 | Lassen et al. |
| 4,743,245 A | 5/1988 | Lassen et al. |
| 4,781,712 A | 11/1988 | Barabino et al. |
| 4,798,603 A | 1/1989 | Meyer et al. |
| 4,804,380 A | 2/1989 | Lassen et al. |
| 4,846,824 A | 7/1989 | Lassen et al. |
| 4,909,244 A | 3/1990 | Quarfoot et al. |
| 4,977,892 A | 12/1990 | Ewall |
| 5,051,259 A | 9/1991 | Olsen et al. |
| 5,114,419 A | 5/1992 | Daniel et al. |
| 5,147,938 A | 9/1992 | Kuller |
| 5,194,299 A | 3/1993 | Fry |
| 5,194,550 A | 3/1993 | Rance et al. |
| 5,221,275 A | 6/1993 | Van Iten |
| 5,277,954 A | 1/1994 | Carpenter et al. |
| 5,369,155 A | 11/1994 | Asmus |
| 5,382,400 A | 1/1995 | Pike et al. |
| 5,387,208 A | 2/1995 | Ashton et al. |
| 5,419,956 A | 5/1995 | Roe |
| 5,445,627 A | 8/1995 | Mizutani et al. |
| H1602 H | 10/1996 | Brock |
| 5,611,790 A | 3/1997 | Osborn, III et al. |
| 5,618,281 A | 4/1997 | Betrabet et al. |
| 5,618,282 A | 4/1997 | Schlangen |
| 5,632,736 A | 5/1997 | Block |
| 5,658,270 A | 8/1997 | Lichstein |
| 5,662,633 A | 9/1997 | Doak et al. |
| 5,669,894 A | 9/1997 | Goldman et al. |
| 5,706,950 A | 1/1998 | Houghton et al. |
| 5,714,225 A | 2/1998 | Hansen et al. |
| 5,759,560 A | 6/1998 | Dillon |
| 5,800,417 A | 9/1998 | Goerg-Wood et al. |
| 5,807,367 A | 9/1998 | Dilnik et al. |
| 5,811,116 A | 9/1998 | Gilman et al. |
| 5,830,202 A | 11/1998 | Bogdanski et al. |
| 5,897,546 A | 4/1999 | Kido et al. |
| 5,910,125 A | 6/1999 | Cummings et al. |
| 5,994,613 A | 11/1999 | Cummings et al. |
| 6,045,900 A | 4/2000 | Haffner et al. |
| 6,080,139 A | 6/2000 | Gallegos |
| 6,156,818 A | 12/2000 | Corzani et al. |
| 6,177,482 B1 | 1/2001 | Cinelli et al. |
| 6,187,989 B1 | 2/2001 | Corzani et al. |
| 6,191,189 B1 | 2/2001 | Cinelli et al. |
| 6,211,263 B1 | 4/2001 | Cinelli et al. |
| 6,213,993 B1 | 4/2001 | Zacharias et al. |
| 6,255,552 B1 | 7/2001 | Cummings et al. |
| 6,316,524 B1 | 11/2001 | Corzani et al. |
| 6,336,935 B1 | 1/2002 | Davis et al. |
| 6,352,528 B1 | 3/2002 | Weber et al. |
| 6,362,389 B1 | 3/2002 | McDowall et al. |
| 6,365,645 B1 | 4/2002 | Cinelli et al. |
| 6,369,126 B1 | 4/2002 | Cinelli et al. |
| 6,386,203 B1 | 5/2002 | Hammerslag |
| 6,495,229 B1 | 12/2002 | Carte et al. |
| 6,566,575 B1 | 5/2003 | Stickels et al. |
| 6,582,411 B1 | 6/2003 | Carstens et al. |
| 6,617,490 B1 | 9/2003 | Chen et al. |
| 6,620,143 B1 | 9/2003 | Zacharias et al. |
| 6,632,210 B1 | 10/2003 | Glasgow et al. |
| 6,641,569 B1 | 11/2003 | Coles et al. |
| 6,657,009 B2 | 12/2003 | Zhou |
| 6,659,990 B1 | 12/2003 | Odorzynski et al. |
| 6,670,402 B1 | 12/2003 | Lee et al. |
| 6,733,483 B2 | 5/2004 | Raufman et al. |
| 6,756,520 B1 | 6/2004 | Krzysik et al. |
| 6,803,420 B2 | 10/2004 | Cleary et al. |
| 6,997,915 B2 | 2/2006 | Gell et al. |
| 7,033,342 B2 | 4/2006 | Mizutani et al. |
| 7,045,559 B2 | 5/2006 | Yahiaoui et al. |
| 7,053,131 B2 | 5/2006 | Ko et al. |
| 7,122,022 B2 | 10/2006 | Drevik |
| 7,125,401 B2 | 10/2006 | Yoshimasa |
| 7,137,971 B2 | 11/2006 | Tanzer |
| 7,198,689 B2 | 4/2007 | Van Gompel et al. |
| 7,217,259 B2 | 5/2007 | McDaniel |
| 7,265,158 B2 | 9/2007 | Risen, Jr. et al. |
| 7,358,282 B2 | 4/2008 | Krueger et al. |
| 7,378,450 B2 | 5/2008 | Erkey et al. |
| 2001/0025163 A1 | 9/2001 | Brown et al. |
| 2001/0039407 A1 | 11/2001 | Widlund |
| 2002/0072725 A1 | 6/2002 | Kolby-Falk |
| 2002/0193766 A1 | 12/2002 | Gell et al. |
| 2003/0004484 A1 | 1/2003 | Hammons et al. |
| 2003/0078554 A1 | 4/2003 | Drevik |
| 2003/0106825 A1 | 6/2003 | Molina et al. |
| 2003/0208112 A1 | 11/2003 | Schmidt et al. |
| 2004/0116883 A1 | 6/2004 | Krautkramer et al. |
| 2004/0122385 A1 | 6/2004 | Morman et al. |
| 2004/0151930 A1 | 8/2004 | Rouns et al. |
| 2004/0167488 A1 | 8/2004 | Bellucci et al. |
| 2004/0167491 A1 | 8/2004 | Mizutani |
| 2004/0209075 A1 | 10/2004 | Maloney |
| 2005/0010185 A1* | 1/2005 | Mizutani et al. ......... 604/385.03 |
| 2005/0014901 A1 | 1/2005 | Osae et al. |
| 2005/0059918 A1 | 3/2005 | Sigurjonsson et al. |
| 2005/0124948 A1 | 6/2005 | Morman et al. |
| 2005/0124960 A1 | 6/2005 | Ruman |
| 2005/0136023 A1 | 6/2005 | Yahiaoui et al. |
| 2005/0136077 A1 | 6/2005 | Yahiaoui et al. |
| 2005/0137549 A1 | 6/2005 | Lindsay et al. |
| 2005/0148984 A1 | 7/2005 | Lindsay et al. |
| 2005/0182378 A1 | 8/2005 | Bonelli et al. |
| 2005/0261652 A1 | 11/2005 | Digiacomantonio et al. |
| 2006/0058760 A1 | 3/2006 | Rosenfeld et al. |
| 2006/0058764 A1 | 3/2006 | Bohlen et al. |
| 2006/0063322 A1 | 3/2006 | Hsu et al. |
| 2006/0079823 A1 | 4/2006 | Utterberg et al. |
| 2006/0089613 A1 | 4/2006 | Mizutani et al. |
| 2006/0129114 A1 | 6/2006 | Mason et al. |
| 2006/0148917 A1 | 7/2006 | Radwanski et al. |
| 2006/0161125 A1 | 7/2006 | Bohlen et al. |
| 2006/0188940 A1 | 8/2006 | Cima et al. |
| 2006/0195053 A1 | 8/2006 | Oelund et al. |
| 2006/0206077 A1 | 9/2006 | Warren et al. |
| 2006/0224133 A1 | 10/2006 | Gannon et al. |
| 2006/0224134 A1 | 10/2006 | Luizzi et al. |
| 2006/0264884 A1 | 11/2006 | Carstens |
| 2007/0100313 A1 | 5/2007 | Luizzi |
| 2007/0124850 A1 | 6/2007 | Buettner |
| 2007/0250028 A1 | 10/2007 | Woltman et al. |
| 2007/0287973 A1 | 12/2007 | Cohen et al. |
| 2008/0021424 A1* | 1/2008 | Erdman ..................... 604/365 |
| 2008/0057811 A1 | 3/2008 | Yahiaoui et al. |
| 2008/0207779 A1 | 8/2008 | Yahiaoui et al. |
| 2008/0234647 A1 | 9/2008 | Arterburn |
| 2009/0036858 A1 | 2/2009 | Van Den Bogart et al. |
| 2009/0054864 A1 | 2/2009 | Lira et al. |
| 2009/0062762 A1 | 3/2009 | Himbergen et al. |
| 2009/0069771 A1 | 3/2009 | Yu et al. |
| 2009/0069780 A1 | 3/2009 | Plentovich et al. |
| 2009/0071862 A2 | 3/2009 | Snell |
| 2009/0171309 A1 | 7/2009 | VanDenBogart et al. |
| 2009/0182296 A1 | 7/2009 | Dennis et al. |
| 2009/0198203 A1 | 8/2009 | Lira et al. |
| 2009/0204090 A1 | 8/2009 | Dennis et al. |
| 2009/0204092 A1 | 8/2009 | Loyd et al. |
| 2010/0121304 A1 | 5/2010 | Zhou et al. |
| 2011/0092945 A1 | 4/2011 | Carstens |

FOREIGN PATENT DOCUMENTS

| | | | |
|---|---|---|---|
| EP | 0 850 628 A1 | | 7/1998 |
| EP | 850628 A1 | * | 7/1998 |
| EP | 0 909 662 A2 | | 4/1999 |
| EP | 0 609 236 B1 | | 5/2002 |
| GB | 2 284 767 A | | 6/1995 |

| | | |
|---|---|---|
| JP | 04-279159 A | 10/1992 |
| KR | 10-2001-0022000 A | 3/2001 |
| KR | 10-0563880 B1 | 3/2006 |
| WO | WO 93/07841 A1 | 4/1993 |
| WO | WO 95/16424 A1 | 6/1995 |
| WO | WO 98/27910 A1 | 7/1998 |
| WO | WO 98/27912 A1 | 7/1998 |
| WO | WO 98/27913 A1 | 7/1998 |
| WO | WO 98/27915 A1 | 7/1998 |
| WO | WO 98/27916 A1 | 7/1998 |
| WO | WO 98/27917 A1 | 7/1998 |
| WO | WO 98/27918 A1 | 7/1998 |
| WO | WO 98/28015 A1 | 7/1998 |
| WO | WO 98/28017 A1 | 7/1998 |
| WO | WO 98/28019 A1 | 7/1998 |
| WO | WO 98/28022 A1 | 7/1998 |
| WO | WO 98/28023 A1 | 7/1998 |
| WO | WO 98/47454 A1 | 10/1998 |
| WO | WO 98/55065 A1 | 12/1998 |
| WO | WO 99/01094 A1 | 1/1999 |
| WO | WO 99/01095 A1 | 1/1999 |
| WO | WO 99/30659 A1 | 6/1999 |
| WO | WO 00/00235 A1 | 1/2000 |
| WO | WO 2006/028612 A1 | 3/2006 |

OTHER PUBLICATIONS

Patent Cooperation Treaty Search Report from the International Search Authority, International Application No. PCT/IB2010/050335 dated Oct. 18, 2010.

Patent Cooperation Treaty Search Report from the International Search Authority, International Application No. PCT/IB2010/050338 dated Oct. 18, 2010.

Patent Cooperation Treaty Search Report from the International Search Authority, International Application No. PCT/IB2010/050407 dated Oct. 21, 2010.

Patent Cooperation Treaty Search Report from the International Search Authority, International Application No. PCT/IB2010/050408 dated Nov. 1, 2010.

Patent Cooperation Treaty Search Report from the International Search Authority, International Application No. PCT/IB2010/050416 dated Nov. 1, 2010.

American Society for Testing Materials (ASTM) Designation: D1300-53 T, "Tentative Specifications and Methods of Test for Laminated Thermosetting Decorative Sheets," pp. 148-166, issued 1953.

"Antiperspirant Drug Products for Over-the-Counter Human Use: Final Monograph," Final Rule, Federal Register—Rules and Regulations, vol. 68, No. 110, Jun. 9, 2003, pp. 34273-34293.

Berner, G. et al. "Photoinitiators—An Overview", Journal of Radiation Curing, vol. 6, No. 2, Apr. 1979, pp. 2-9.

Lloyd, Jillian et al., "Female Genital Appearance: 'Normality' Unfolds," BJOG: An International Journal of Obstetrics and Gynecology, vol. 112, May 2005, pp. 643-646.

Mandavi, Alborz et al., "A Biodegradable and Biocompatible Gecko-Inspired Tissue Adhesive," PNAS, vol. 105, No. 7, Feb. 19, 2008, pp. 2307-2312.

* cited by examiner

DYNAMIC FITTING BODY ADHERING ABSORBENT ARTICLE

CROSS REFERENCE TO RELATED APPLICATIONS

This application is a continuation-in-part of U.S. patent application Ser. No. 12/364,486 filed Feb. 2, 2009, which is a continuation-in-part of U.S. patent application Ser. No. 11/890,093 filed Aug. 3, 2007 and of U.S. patent application Ser. No. 12/005,793 filed Dec. 28, 2007 now U.S. Pat. No. 7,947,027. Each of these applications is hereby incorporated by reference in its entirety.

BACKGROUND

Personal care articles are well known in the art. Such articles can desirably be disposable. Such articles can also be absorbent and can absorb discharged bodily fluids from a user. Such absorbent articles generally comprise a fibrous mass or other absorbent structure which can absorb and hold body fluids. Similarly, it is well known that feminine care articles have been employed to absorb and hold liquids, such as urine and/or menses and/or other complex fluids. A typical structure of an absorbent article includes a fluid impermeable backsheet, a fluid permeable topsheet and an absorbent core positioned between the backsheet and the topsheet. Prior absorbent articles have also included various other features to improve fluid handling, such as intake layers, distribution layers, retention layers and the like. In these absorbent personal care articles, the topsheet is the body-facing side of the absorbent article and the backsheet is the garment-facing side of the absorbent article.

Generally, such absorbent articles are held in place during use by using the wearer's waist and elastic materials in the waist portion of the articles, in the case of pant-like garments, such as diapers and training pants, or by attaching the absorbent article to the underwear or undergarment of a wearer, in the case of pads or liners. Current methods of attaching the absorbent article to the underwear or undergarment of a wearer include placing an adhesive on the garment-facing side of the backsheet, having optional flaps (also called wings or side panels) that extend from the longitudinal sides of the absorbent article which wrap around the crotch portion of the underwear or undergarment of the wearer, and a combination of the adhesive and the flaps.

It has also been suggested to use an adhesive to adhere the absorbent article to the skin of the wearer. However, the design of these absorbent articles was essentially the same as the absorbent articles which were attached to the underwear or undergarment of the wearer. That is, the adhesive is applied to the body-facing surface of the topsheet of the absorbent structure. Alternatively, in another design, a portion of the backsheet of the absorbent structure was wrapped around and over the topsheet. This portion of the backsheet which is wrapped around and over the topsheet of the absorbent structure then becomes a body-facing surface. An adhesive is applied to the portion of the backsheet which is wrapped over the topsheet. While these designs were effective for adhering the absorbent article to the skin of a wearer, these absorbent articles were not comfortable for wearers to wear, since the shape and size of such absorbent articles were the same as those absorbent articles which were attached to the undergarment or underwear of the wearer. Furthermore, if the adhering portion came into contact with any hair in the region, such as pubic hair, removal of the garment could be excruciatingly painful to the user.

Similarly, absorbent articles that are attached to the underwear or undergarment of a wearer can also be uncomfortable for the wearer. This is because during normal movement of the body, portions of the body place opposed forces on the undergarment, which may cause the undergarment to be bunched or twisted. When this occurs, any absorbent article attached to the underwear or undergarment may also become bunched or twisted, causing discomfort to the wearer of the absorbent article. For example, the presence and absence of pressure from the absorbent article on the inner thighs as the wearer moves, which is often described by wearers as feeling "like a diaper", is one source which compromises comfort and confidence for wearers of conventional absorbent articles, including liners, ultra-thin absorbent pads and maxi pads, for example. In addition, the movement of the wearer or deformation of the underwear while being worn may also cause the absorbent article to have a poor fit against the body of the wearer, which could result in leaks from the absorbent article.

Another disadvantage of conventional absorbent articles is that the silhouette or outline of the absorbent article may be visible to others through the clothing of the wearer. Even currently available ultra-thin absorbent articles may be visible through tight fitting outer clothing of a wearer. Therefore, conventional absorbent personal care articles do not always provide discretion for wearers.

There is a need in the art to provide wearers of absorbent articles with a discrete article which can function as an undergarment if desired, is as easy to use as a conventional pad and is comfortable to wear, and will effectively prevent or reduce premature leakage during use. A suitable body adhering absorbent article in the form of a feminine pad having an absorbent structure adhered to an extensible body adhering shell is described in U.S. patent application Ser. No. 11/890, 093 filed Aug. 3, 2007, and U.S. patent application Ser. No. 12/364,486 filed Feb. 2, 2009, each of which is incorporated by reference in manner that is consistent herewith. However, it has been discovered that a disadvantage of such pad is that it may not always provide a desirably snug fit with minimal gaps for a wide range of consumers over the entire range of movement. This is particularly apparent when the absorbent structure is adhered to the shell primarily throughout its entire length, which consequently limits extension in the posterior half of the shell. Another disadvantage is that the attachment adhesive located on the absorbent structure utilized for attaching the absorbent structure to the shell extends past the peripheral edge of the shell. Such an arrangement results in exposed adhesive which can cause discomfort for the wearer of the article. Thus, there is a further need for a body adhering absorbent article that provides a snug fit with minimal gaps for a wide range of consumers over the entire range of movement.

SUMMARY

In response to the needs discussed above, a disposable article of the present invention provides a body-adhering absorbent article having a shell composition, absorbent structure composition, shell shape and properties, shell application, body attachment means, stretch properties, and absorbent structure attachment to the shell which provides a comfortable, discreet and snug fit with minimal gaps for a wide range of consumers over the entire range of movement.

In some aspects, a disposable personal care article comprises a shell having a unitary structure for disposition adjacent a wearer's vulva region, where the shell has a first side and a second side, the first side having a first area and a second area. The first area of the shell contacts to the wearer's skin and/or hair surrounding the vulva region. At least a portion of the first area comprises a body attachment means for adhering the shell directly to the skin and/or hair of the wearer. In addition, the shell has an anterior half and a posterior half where the posterior half exhibits a higher extension relative to the anterior half when a stretching force of 454 grams is applied, as measured by the % Strain Differential Test. In further aspects, the shell comprises a woven web, nonwoven web, a gel, a film, a sheet of a polymeric material, a foam, or a laminate. In other aspects, the shell comprises a silicone material. In yet other aspects, the first area of the shell has an anterior half and a posterior half, wherein at least a portion of the anterior half of the shell and at least a portion of the posterior half of the shell each comprise body adhesive properties, wherein the body adhesive properties provide a means to attach the personal care article directly to the wearer's body. In still other aspects, the shell has an anterior half and a posterior half, wherein at least a portion of the posterior half is adapted to attach to the body of a wearer between the vulva region and the coccyx of the body of the wearer and at least a portion of the anterior half is adapted to attach to the pubic area above the vulva region of the wearer. In yet other aspects, the shell is breathable. In still other aspects, the shell comprises material that is selected from extensible or elastically extensible materials, or combinations thereof. In yet other aspects, at least a portion of the first area of the shell further comprises at least one of a release sheet, a carrier sheet, or an ATL. In still other aspects, the body attachment means and shell form a body attachment means/shell composite having a higher stiffness and/or a lower stretch than the remainder of the shell. In further aspects, the anterior absorbent structure attachment is a permanent attachment means, and the posterior absorbent structure attachment is a refastenable attachment means. In yet other aspects, the body attachment means is an adhesive.

In some aspects, the disposable personal care article further comprises an absorbent structure configured for disposition adjacent a wearer's vulva region. The absorbent structure has an anterior half and a posterior half. The absorbent structure is present in the second area of the shell. The absorbent structure is attached to the shell via an absorbent structure attachment means in the anterior half and in the posterior half of the absorbent structure. In addition, the absorbent structure attachment means is selected from an anterior point bond, a posterior point bond or a U-shaped attachment, or combinations thereof. In other aspects, the disposable personal care article has an anterior point bond and a posterior point bond, wherein the anterior point bond has a coverage area of about 5 mm$^2$-about 200 mm$^2$ and the posterior point bond has a coverage area of about 5 mm$^2$-about 200 mm$^2$, where the bonds are longitudinally aligned along the longitudinal centerline of the personal care article and where the anterior point bond and the posterior point bond are separated by a distance of at least about 5 mm. In yet other aspects, the absorbent structure is at least partially free-floating. In still other aspects, the absorbent structure further comprises at least one of a topsheet, a backsheet, a surge layer or a transfer layer. In yet other aspects, the disposable personal care article further comprises at least one of an absorbent structure positioning aid, an article positioning aid, or an article removal aid. In still other aspects, the shell further comprises an absorbent material. In yet other aspects, the absorbent structure attachment means is present as an anterior absorbent structure attachment means and a posterior absorbent structure attachment means, where the anterior absorbent structure attachment means is a permanent attachment and the posterior absorbent structure attachment means is a refastenable attachment, and where the force required to sever the refastenable attachment is less than the knee point of shell. In still other aspects, the shell has a lower coefficient of friction than the adjacent surface of a garment with which the shell comes in contact with.

In some aspects, the personal care article is selected from a pantiliner, a sanitary napkin, a maxi-pad or an incontinence article.

Numerous other features and advantages of the present invention will appear from the following description. In the description, reference is made to exemplary aspects of the invention. Such aspects do not represent the full scope of the invention. Reference should therefore be made to the claims herein for interpreting the full scope of the invention. In the interest of brevity and conciseness, any ranges of values set forth in this specification contemplate all values within the range and are to be construed as support for claims reciting any sub-ranges having endpoints which are real number values within the specified range in question. By way of a hypothetical illustrative example, a disclosure in this specification of a range of from 1 to 5 shall be considered to support claims to any of the following ranges: 1-5; 1-4; 1-3; 1-2; 2-5; 2-4; 2-3; 3-5; 3-4; and 4-5.

BRIEF DESCRIPTION OF THE DRAWINGS

The foregoing and other features, aspects and advantages of the present invention will become better understood with regard to the following descriptions, appended claims and accompanying drawings where:

Figure 1:
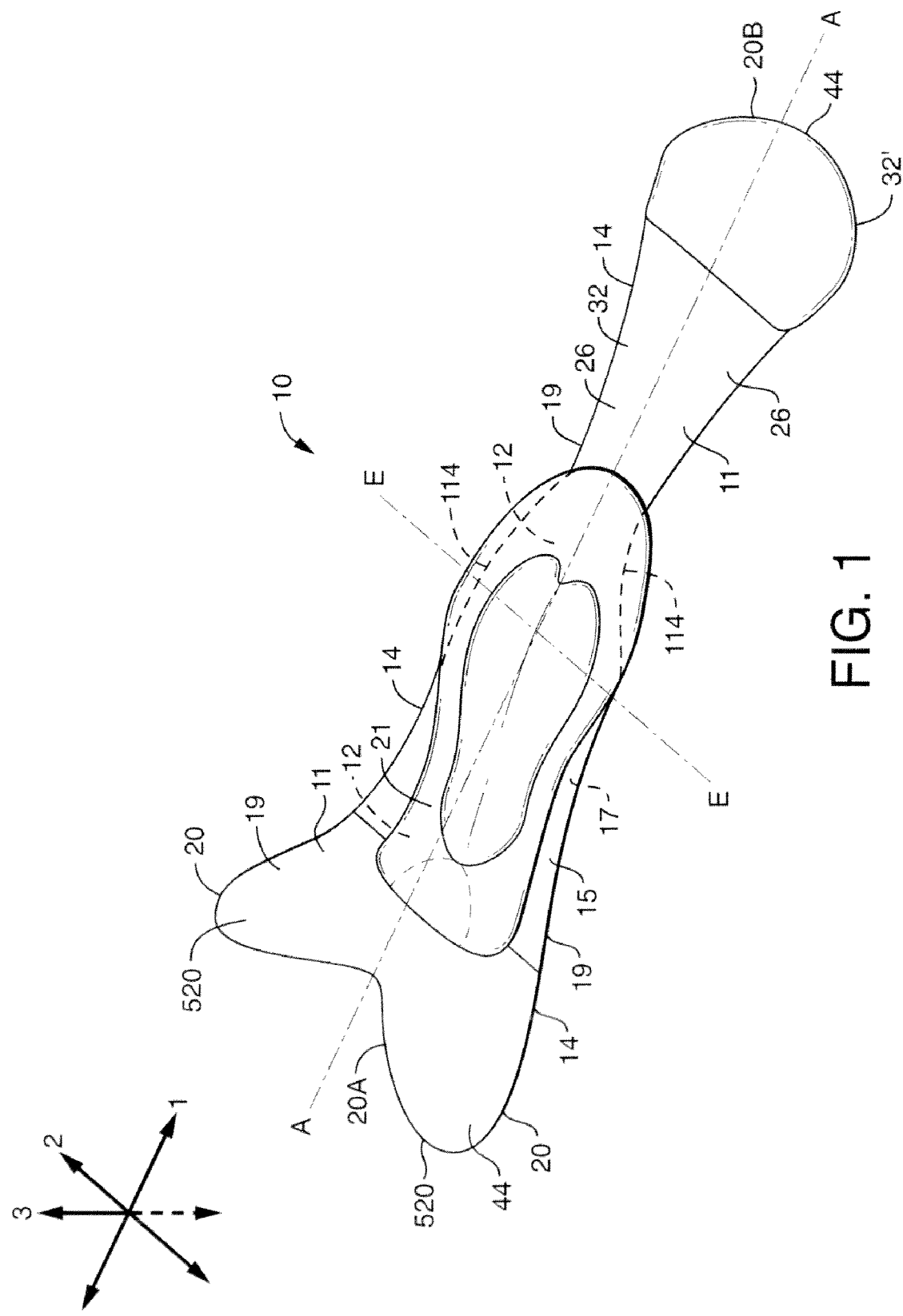
FIG. 1 shows a perspective view of one aspect of the article having a shell and an absorbent structure.

Repeated use of reference characters in the present specification and drawings is intended to represent the same or analogous features or elements of the present invention. The drawings are representational and are not necessarily drawn to scale. Certain proportions thereof may be exaggerated, while others may be minimized.

Test Methods

% Strain Differential Test

Figure 22:
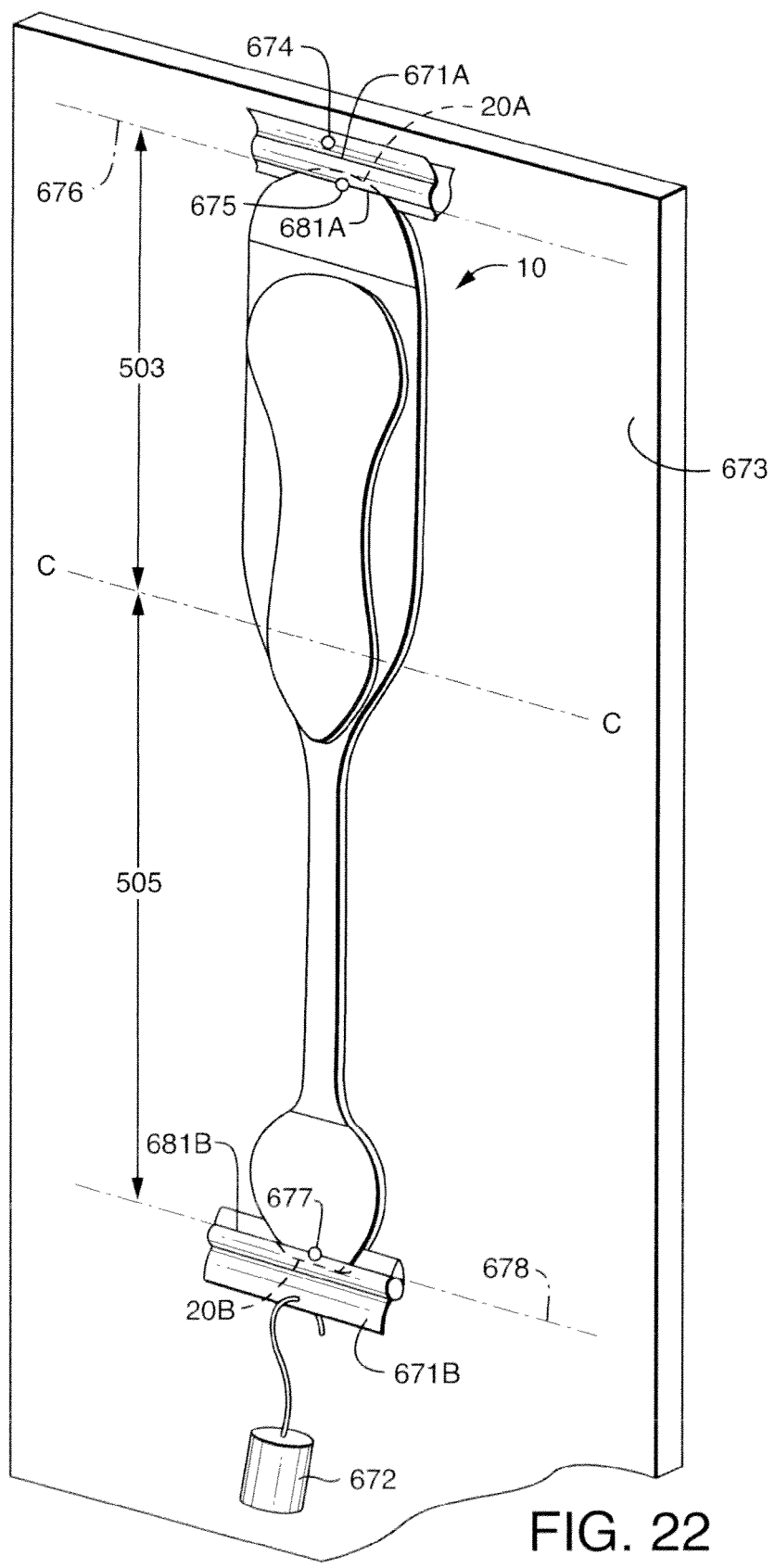
FIG. 22 is a device for measuring % Strain Differential.

This test determines the % strain differential of anterior and posterior halves (503 and 505, respectively) of the disposable personal care article of the present invention at a specified load. Reference is made to FIG. 22.

The following materials are required:

Two 7.6-cm Bulldog clips 671A and 671B that are approximately 44 grams each;

A 452 gram weight with hook 672;

A 30.5 cm×61.0 cm plexiglass hanging board 673;

A securement screw 674;

A stop watch that can measure in seconds (not shown); and

A 61.0 cm ruler that can measure in millimeters (not shown).

Equipment Assembly of the Apparatus 670:

Secure one of the bulldog clips 671A to the board 673 with the securement screw 674. Then position the hanging board 673 so that it is in the vertical position, as shown in FIG. 22.

Test Procedure:

Provide the test sample 10. Mark a lateral line at the longitudinal center of the article 10 (denoted in the illustration as line C-C). Measure 10 mm from the furthest extent of anterior longitudinal edge 20A. This point is identified as point 675. On the test sample 10 mark a lateral line 676 intersecting point 675. Measure 10 mm from the furthest extent of posterior edge 20B of the test sample. This point is identified as point 677. On the test sample 10 make a lateral line 678 intersecting point 677. Secure the body adhering absorbent article 10 in the jaws of the bulldog clip 671A that is secured to the hanging board 673 so that line 676 is adjacent to the edges 681A of the bull dog clip 671A with the majority of the product dangling below. Apply the second unsecured bulldog clip 671B so that line 678 is adjacent to the clamping edges 681B of the bull dog clip 671B with the majority of the product 10 suspended between the bulldog clips 671A,671B. Allow the unsecured bulldog clip 671B to hang vertically without support applying initial stress of approximately 44 grams to the body adhering article 10 for 60 seconds using the stopwatch. Measure the length of the product between the bulldog clip edges (681A,681B) using the ruler. This is dimension A-Int. Next, determine dimensions 503-Int and 505-Int by using the following equation:

$$503Int=505Int=(20\ mm+(\text{dimension } A\text{-}Int))/2$$

Apply the 452 gram weight 672 to the free hanging bulldog clip 671B. Wait for 60 seconds using the stopwatch. Then, measure the length between the centerline (line C-C) and the unsecured bulldog clip edge 681B using the ruler. This is the dimension 505Aft.

Determine dimension 505Fin using the following equation:

$$505Fin=(505Aft+10\ mm)$$

Measure the length between the secured bulldog clip edge 681A and centerline (line C-C) using the ruler. This is the dimension 503Aft. Determine dimension 503Fin by using the following equation:

$$503Fin=(503Aft+10\ mm)$$

Determine the % Strain Differential between anterior half 503 and the posterior half 505 of the body adhering absorbent article 10 by using the following equation:

$$\%\ \text{Strain Differential}=((505Fin-503Fin)/(503Fin))\times 100\%$$

Determine the % Extension of posterior half 505 relative to the anterior half 503 of the body adhering absorbent article 10 by using the following equation:

$$\%\ \text{Extension}=[((505Fin-505Int)-(503Fin-503Int))/(503Fin-503Int)]\times 100\%$$

Light Transmittance Test

Light transmittance (also referred to herein as light transmission) is measured consistent with ASTM D-1300 utilizing a GARDNER HAZE GUARD PLUS Model #4725 (available from BYK Gardner, having a place of business located in Columbia, Md., U.S.A.). In particular, a flat sample of the material to be tested is placed in the round holder having approximately a 60 mm diameter. Measurements are then taken by placing the flat sample in the measuring port. The haze port is used for measuring light transmittance. A series of five samples are measured and the average value of the five samples provides the light transmittance. Haze and clarity may also be measured using the GARDNER HAZE GUARD PLUS unit.

Coefficient of Friction Test (ASTM D-1894-78)

This test method covers determination of the coefficient of sliding friction of the shell material when sliding over itself or other substances at specified test conditions.

Generally, the apparatus used to carry out the test method includes a sled made of a metal block 63.5 mm (2.5 inches) square by approximately 6 mm (0.25 inch) thick with a suitable eye screw fastened in one end. In addition, a polished plastic, wood, or metal sheet, approximately 150 by 300 by 1 mm (6 by 12 by 0.040 inch) is used as a plane. A smooth, flat piece of glass may cover the upper surface of the plane, thereby providing a smooth support for the specimen. Other materials include scissors or a cutter suitable for cutting specimens to the desired dimensions, adhesive tape such as cellophane or pressure-sensitive tape, and double-faced adhesive tape. Additional materials include a nylon monofilament, having a 0.33±0.05 mm (0.013±10.002 inch) diameter and capable of supporting a 3.6 kg (8 pound) load, low-friction pulleys such as a phenolic type pulley mounted in hardened steel cone bearings on a metal fork, or a ball-bearing type pulley may be used, and a force-measuring device capable of measuring the frictional force to ±5% of its value, for example a spring gage, a universal testing machine or a strain gage may be used. Other equipment includes a supporting base. A smooth wood or metal base approximately 200 mm by 380 mm (8 by 15 inches) is necessary to support the plane. The supporting base may be a simple rectangular box. A driving or pulling device for the sled or plane is also needed. The plane may be pulled by a driven pair of rubber-coated rolls not less than 200 mm (8 inches) long, capable of maintaining a uniform surface speed of 150±30 mm/min (0.5±0.1 ft/min) by the crosshead of a universal testing machine, or a worm drive driven with a synchronous motor. A constant-speed chain drive system can also be used. A power-operated source may be used for pulling the sled over the horizontally-mounted specimen at a uniform speed of 150±30 mm/min (0.5±0.1 ft/min).

The test specimen that is to be attached to the plane should be cut approximately 250 mm (10 inches) in the longitudinal direction and 130 mm (5 inches) in the transverse direction when such extrusion directions exist and are identifiable.

The test method is carried out by taping the edge of the test specimen to a plane with the longitudinal direction of the specimen in the 250-mm direction. Smooth the specimen to eliminate wrinkles if necessary, taking care not to alter the specimen surface through finger oils, etc. For film specimens, tape the edges of the film specimen to the back of the sled, using adhesive tape and pulling the specimen tight to eliminate wrinkles without stretching it. For sheet specimens, tape the sheet specimen to the sled face with double-faced tape. Keep the longitudinal direction of the specimen parallel to the length of the sled (where such direction exists and is identifiable).

Next, attach the specimen-covered sled through its eye screw to the nylon filament. If a universal testing machine is used, pass the filament through the pulley(s) and upward to the bottom of the load-sensing device and attach securely. If a spring gage is used, securely attach the filament to it. The nylon filament shall be of sufficient length to allow maximum sled or plane travel. With some slack in the nylon filament, lightly place the sled in position on the horizontal plane. The positioning of the sled shall be such that the length of the sled, the adjacent length of nylon filament, and the long dimension (longitudinal direction) of the plane-mounted specimen are parallel.

Start the driving mechanism (which has been adjusted previously to provide a speed of 150±30 mm/min (0.5±0.1 ft/min)). As a result of the frictional force between the contacting surfaces, no immediate relative motion may take place between the sled and the moving plane until the pull on the sled is equal to, or exceeds the static frictional force acting at the contact surfaces. Record the visual average reading during a run of approximately 130 mm (5 inches) while the surfaces are sliding uniformly over one another. This is equivalent to the kinetic force required to sustain motion between the surfaces and normally is lower than the static force required to initiate motion. After the sled has traveled over 130 mm (5 inches) stop the apparatus and return to the starting position.

If a strain gage and load-displacement recorder are used, either draw the best straight line midway between the maximum points and minimum points shown on the chart while the sled was in motion, or obtain the average load by integration of the recorder trace. The mean load is the kinetic friction force required to sustain motion on the sled.

Remove the test specimen from the sled and the horizontal plane. The apparatus is now ready for the next set of specimens. A new set of specimens shall be used for each run.

Calculate the coefficient of friction, $\mu_k$, as follows:

$$\mu_k = A_k/B$$

where:

$A_k$=average scale reading obtained during uniform sliding of the film surfaces, and B=sled weight.

DEFINITIONS

It should be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

It should be understood that the term "absorbent product" or "absorbent article", as used herein, refers to any article used to control bodily fluids that are configured to absorb and retain bodily exudates, including urine, blood, menses, and other bodily discharges, such as sweat and vaginal secretions resulting from sexual activity and the like. In addition, the term is intended to include odor absorbing articles.

As used herein, the term "absorbent structure" is intended to mean a configuration of an absorbent material which allows fluids to be absorbed by the absorbent material. As used herein, an absorbent structure of the present invention does not include the shell.

As used herein, the term "anterior" refers to the direction towards the front of the wearer during use.

As used herein, the term "attach" and its derivatives refer to the joining, adhering, connecting, bonding, sewing together, or the like, of two elements. Two elements will be considered to be attached together when they are integral with one another or attached directly to one another or indirectly to one another, such as when each is directly attached to intermediate elements. "Attach" and its derivatives include permanent, releasable, or a refastenable attachment. In addition, the attachment can be completed either during the manufacturing process or by the end wearer.

As used herein, "body-facing" means that surface or side of the article which is intended to be disposed toward or placed adjacent to the body of the wearer during ordinary use. The term "garment-facing" means that surface or side that is on the opposite side of the article from the body-facing surface or side. The garment-facing surface is an outward surface of the article and is intended to be disposed to face away from the wearer's body during ordinary use. The garment-facing surface is generally arranged to face toward or placed adjacent to the wearer's undergarments or clothing when the article is worn.

The term "coform" refers to a blend of meltblown fibers and absorbent fibers such as cellulosic fibers that can be formed by air forming a meltblown polymer material while simultaneously blowing air-suspended fibers into the stream of meltblown fibers. The coform material may also include other materials, such as superabsorbent materials. The meltblown fibers and absorbent fibers (and other optional materials) are collected on a forming surface, such as provided by a foraminous belt. The forming surface may include a gas-pervious material that has been placed onto the forming surface.

The term "complex liquid" describes a liquid generally characterized as being a viscoelastic liquid comprising multiple components having inhomogeneous physical and/or chemical properties. It is the inhomogeneous properties of the multiple components that challenge the efficacy of an absorbent or adsorbent material in the handling of complex liquids. In contrast with complex liquids, simple liquids, such as, for example, urine, physiological saline, water and the like, are generally characterized as being relatively low-viscosity and comprising one or more components having homogeneous physical and/or chemical properties. As a result of having homogeneous properties, the one or more components of simple liquids behave substantially similarly during absorption or adsorption, although some components of the simple liquids may be absorbed or adsorbed more readily than others. Although a complex liquid is generally characterized herein as including specific components having inhomogeneous properties, each specific component of a complex liquid generally has homogeneous properties. Consider for example a representative complex body-liquid having three specific components: red blood cells, blood protein molecules and water molecules. Upon examination, one skilled in the art could easily distinguish between each of the three specific components according to their generally inhomogeneous properties. Moreover, when examining a particular specific component such as the red blood cell component, one skilled in the art could easily recognize the generally homogeneous properties of the red blood cells.

As used herein, the term "connected" is intended to mean directly connected and indirectly connected. By directly connected, it is intended that the connected elements are in contact with one another or affixed to one another. By indirectly connected, it is intended that one or more intervening or intermediate elements are between the two elements which are secured or "connected" together. The intervening elements may be affixed.

As used herein, the term "disposable" is used herein to describe personal care articles that are not intended to be laundered or otherwise restored or reused as a personal care article after a single use.

Unless otherwise defined in the specification, the terms "elastomeric," "elastic" and variations thereof, refer to a material that can be stretched without breaking by at least 50% (to least 150% of its initial un-stretched length) in at least one direction and which, upon release of stretching will recover at least 30% of its elongation within about one minute. The term "extensible" refers to a material that may be stretched by at least about 50% in one or more directions. The term "inelastic" refers to materials that do not stretch by 50% or more and to materials that stretch by that amount but do not retract by more than 30%. Inelastic materials also include materials that do not extend, e.g., which tear, when exposed to a stretching force.

Figure 17:
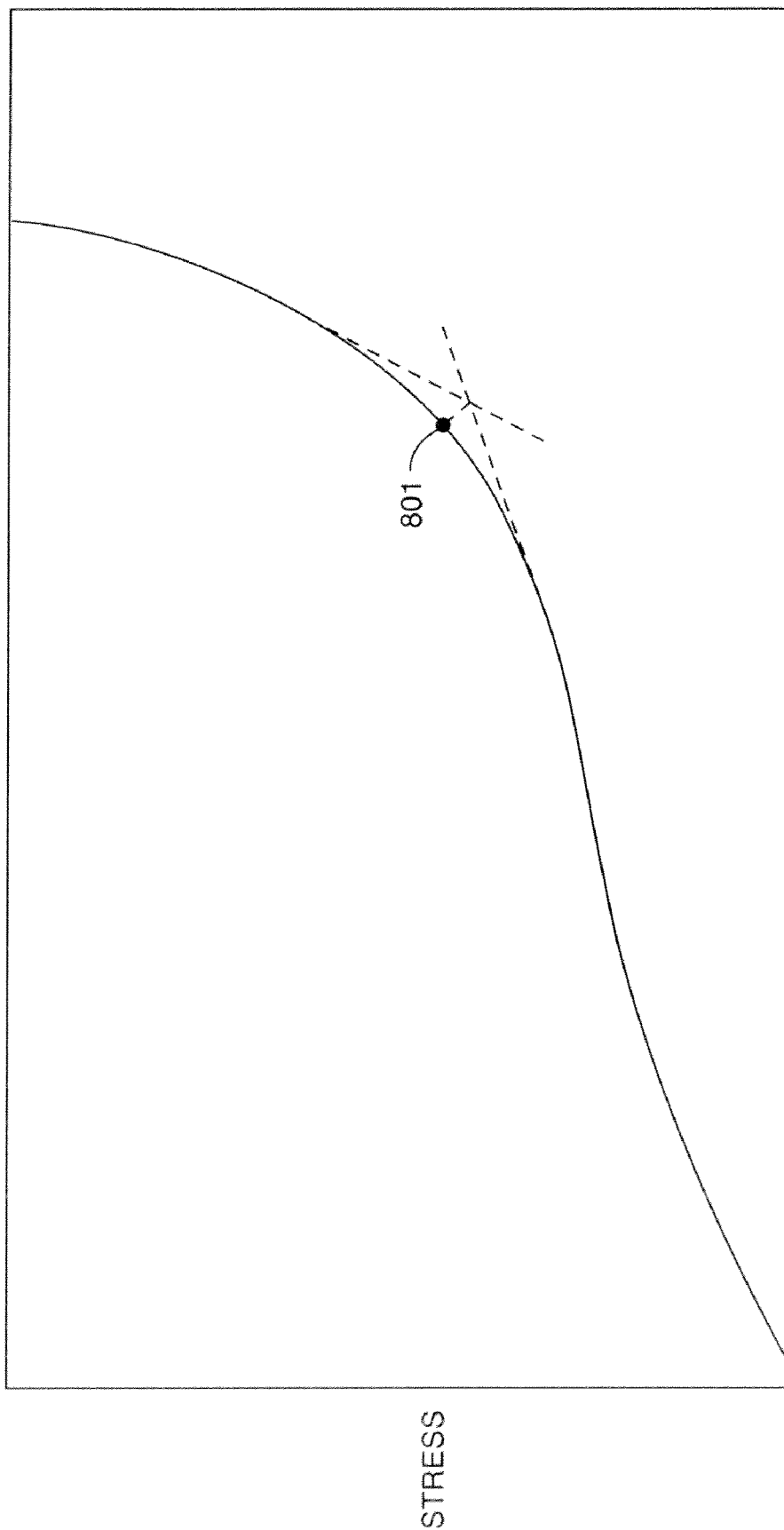
FIG. 17 is a graphical representation of a stress/strain curve and showing a knee point.

As used herein, the term "knee point" refers to tangent lines that are drawn on either side of the concave portion of a stress/strain curve. A point is identified by the intersection of these two lines. A line is then drawn that intersects that point and which is perpendicular to the stress/strain curve. Where this line intersects the stress/strain curve identifies a point which is the knee point of the curve. This is illustrated in FIG. 17 as element 801.

As used herein, the term "liquid impermeable," when used in describing a layer or multi-layer laminate means that liquid, such as urine, menses or bowel movement, will not pass through the layer or laminate, under ordinary use conditions, in a direction generally perpendicular to the plane of the layer or laminate at the point of liquid contact.

As used herein, the term "liquid permeable" refers to any material that is not liquid impermeable.

As used herein, the terms "nonwoven" and "nonwoven web" refer to materials and webs of material having a structure of individual fibers or filaments which are interlaid, but not in an identifiable manner as in a knitted fabric. The terms "fiber" and "filament" are used herein interchangeably. Nonwoven fabrics or webs have been formed from many processes such as, for example, meltblowing processes, spunbonding processes, air laying processes, and bonded-carded-web processes. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91.)

As used herein, the term "personal care article" includes, but is not limited to, articles such as diapers, diaper pants, baby wipes, training pants, absorbent underpants, child care pants, swimwear, and other disposable garments; feminine care products including sanitary napkins, wipes, menstrual pads, menstrual pants, pantiliners, panty shields, interlabials, tampons, and tampon applicators; adult-care products including wipes, pads such as breast pads, containers, incontinence products, and urinary shields; clothing components; bibs; athletic and recreation products; and the like.

As used herein, the term "polymer" generally includes, but is not limited to, homopolymers, copolymers, such as for example, block, graft, random and alternating copolymers, terpolymers, etc., and blends and modifications thereof. Furthermore, unless otherwise specifically limited, the term "polymer" shall include all possible geometrical configurations of the material. These configurations include, but are not limited to, isotactic, syndiotactic and random symmetries.

As used herein, the term "posterior" refers to the direction towards the back of the wearer during use.

As used herein, the term "superabsorbent material" refers to a water-swellable, generally water-insoluble, hydrogel-forming polymeric absorbent material, which is capable of absorbing at least about 10, suitably about 30, and possibly about 60 times or more its weight in physiological saline (e.g., saline with 0.9 wt % NaCl). In contrast, the term "absorbent material" refers to a material that is capable of absorbing at least about 5 times or more its weight in physiological saline (e.g., saline with 0.9 wt % NaCl). In the case of complex fluids, the term "superabsorbent material" refers to a water-swellable, generally water-insoluble, hydrogel-forming polymeric absorbent material, which is capable of absorbing at least about 10 times or more its weight in menses simulant (i.e., menses simulant composed of swine blood diluted with swine plasma to provide a hematocrit level of 35% (by volume), suitably HEMATOSTAT-2, available from Separation Technology, Inc., a business having offices located in Altamonte Springs, Fla., U.S.A.).

DETAILED DESCRIPTION

The product of the present invention provides a personal care article which is designed to adhere to the body of a wearer in the area of the body which may need bodily fluids controlled. In one particular aspect, the article is a disposable personal care absorbent article that is attached to the body of a female wearer to or around the vulva region of the body. By "to or around the vulva region," it is meant adjacent regions of the body of a female including the pubic region and the perinea region up to and including the coccyx.

When applied to or around the vulva region of the female body, the personal care article may be used as a pantiliner, sanitary napkin or incontinence article, for example. In addition, in some aspects, the article may be worn as an underwear substitute since the article of the present invention does not need underwear to hold the article in place. As an underwear substitute, the article provides protection to the vulva area by creating a barrier between the outer clothing and the vulva region of a wearer. In some aspects, the article is a disposable article that can provide a means for attaching or changing out an absorbent structure during use. In contrast, a woven undergarment, such as underwear, is not considered to be a disposable article since it is intended to be laundered and worn again. The article of the present invention can serve to protect the outer clothing of the wearer from bodily discharges from the vulva region, and optionally other regions (e.g., the perinea region) of the wearer's body. In other aspects, the article can serve to protect the sensitive skin and body features of the vulva region from roughness of outer or adjacent garments or clothing, thereby preventing or alleviating irritation to the sensitive skin and body features of at least the vulva region.

Figure 2:
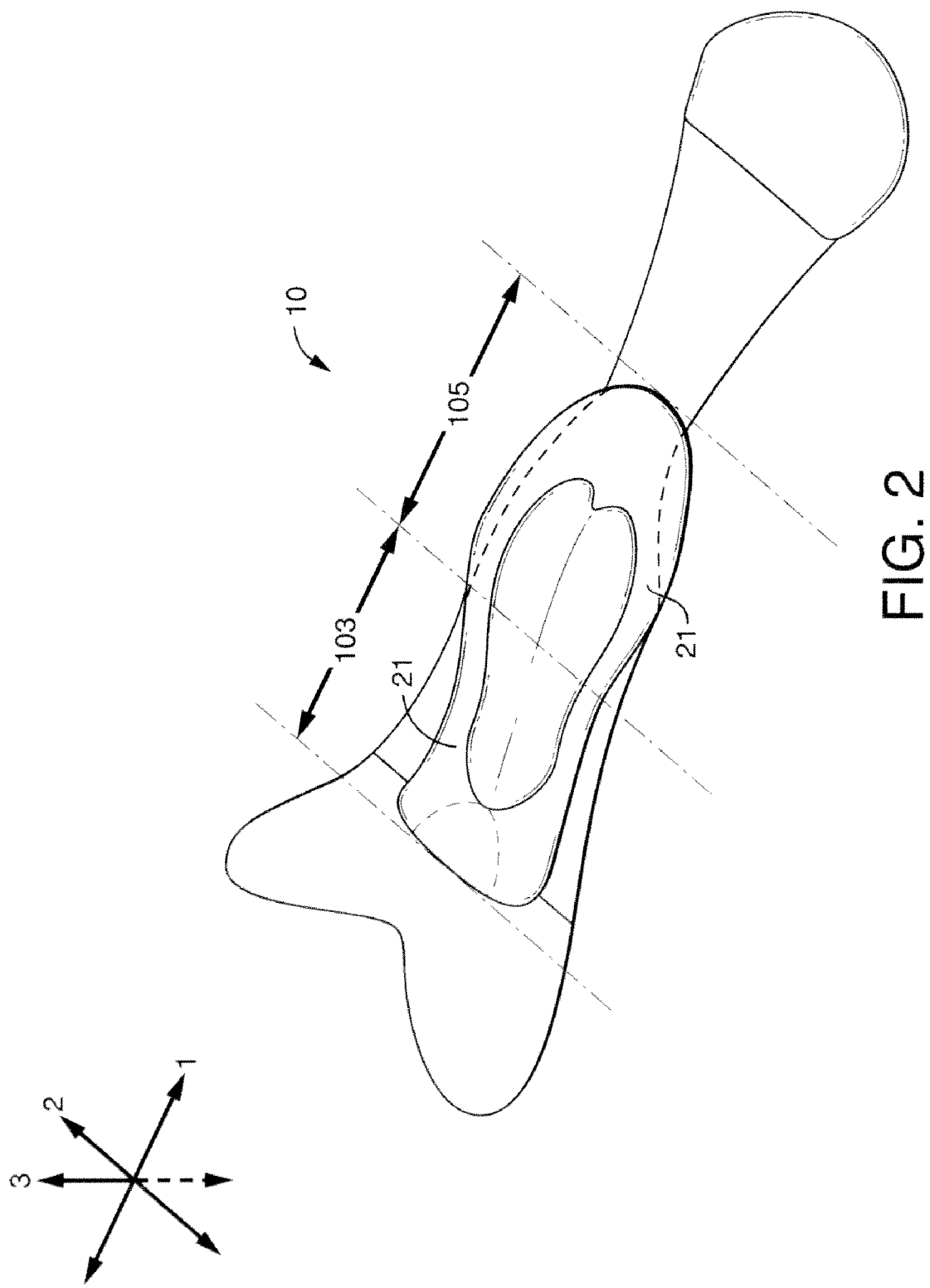
FIG. 2 shows a perspective view of one aspect of the article having a shell and an absorbent structure with portions.
Figure 3:
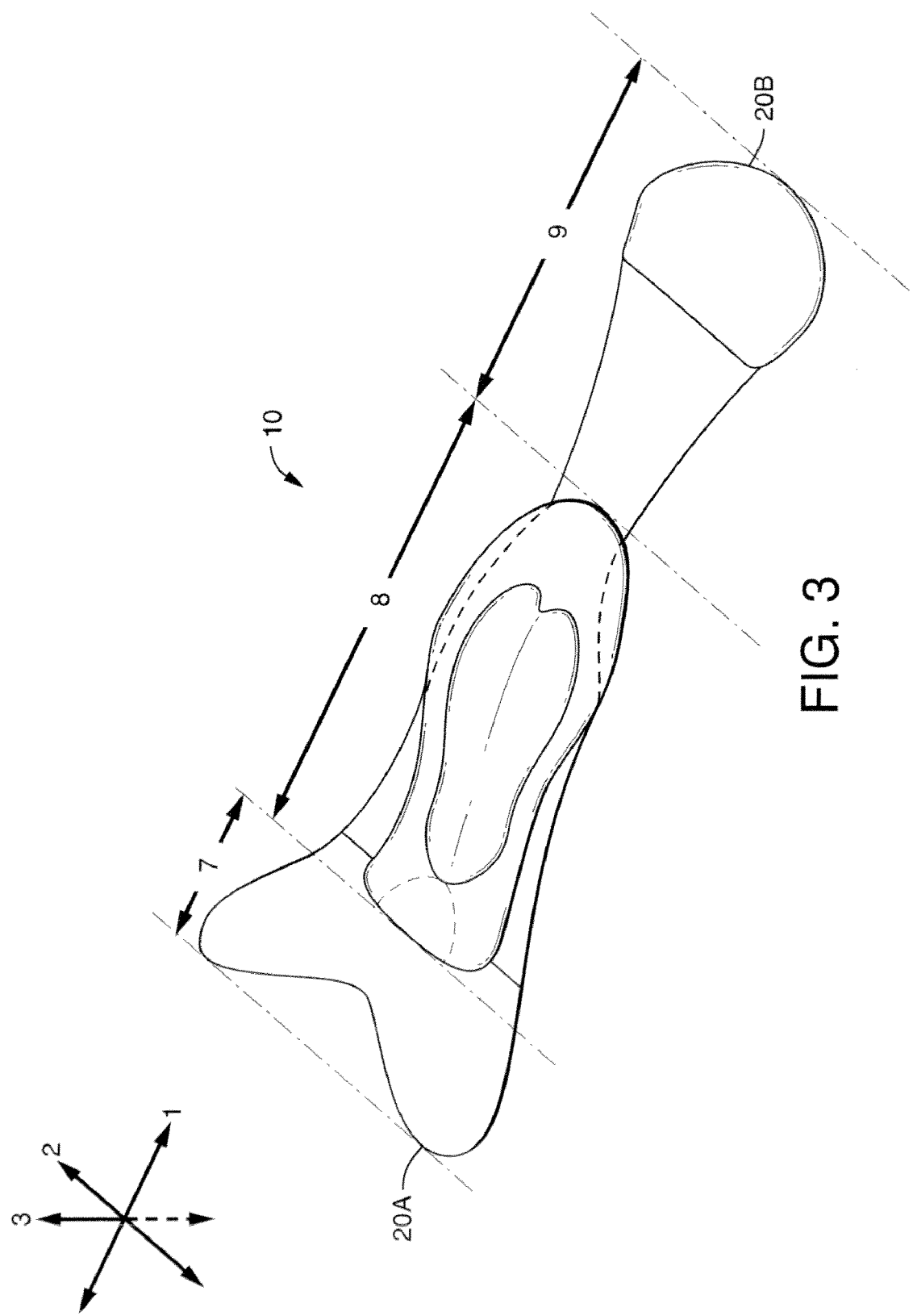
FIG. 3 shows a perspective view of one aspect of the article having regions.

To gain a better understanding of the present invention, attention is directed to the Figures of the present specification. As is shown in FIGS. 1-3, one aspect of the article 10 has a longitudinal direction (x-direction) 1 a lateral direction (y-direction) 2 and a z-direction 3. One component of the personal care article is a shell 14. This shell 14 has a first side 15 and a second side 17, as is shown in FIG. 1. In desirable aspects, the shell 14 is a single contiguous structure. The shell 14 can help to provide the overall contour or silhouette of the article of the present invention. In addition, the shell 14 can also provide a surface for attachment or adhesion of the article 10 to the body of a wearer. In some desirable aspects, the shell 14 also provides a surface for attachment or adhesion of an absorbent structure 21, either prior to or during use.

The first side 15 of the shell 14 is the body-facing side of the article 10 and the second side 17 of the shell 14 is the garment-facing (or outward-facing) side of the article. By "outward facing side," it is meant the side which does not face toward body of the user. The first side 15 of the shell 14 has a first area 11 and a second area 12. The first area 11 is adjacent to, and in contact with, the second area 12, as is shown in FIG. 1. The second area 12 defines the portion of the shell 14 that is covered by the absorbent structure 21, when present. The first area 11 defines the portion of the shell 14 that is not covered by the absorbent structure when the absorbent structure 21 is in place.

Figure 9:
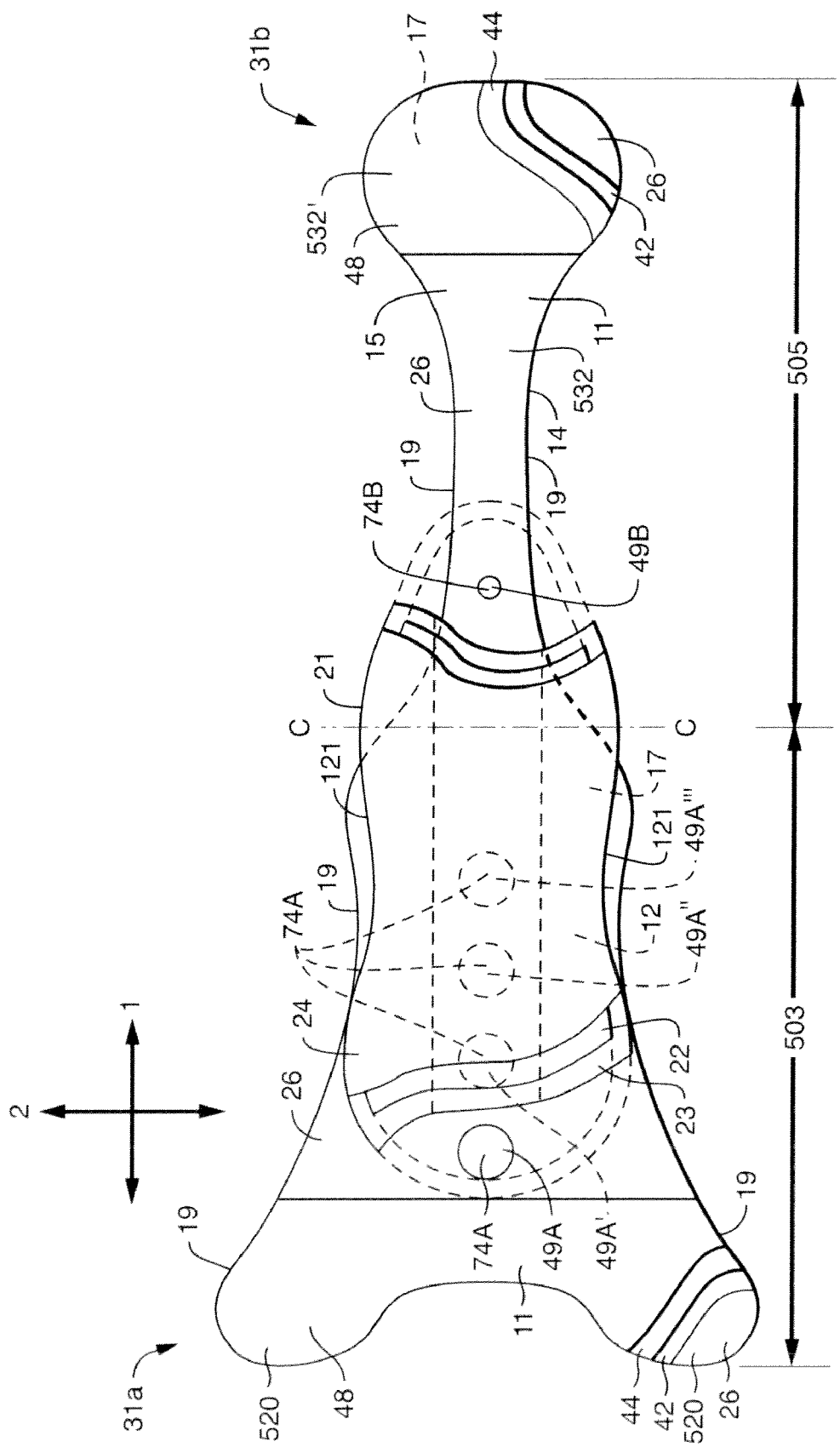
FIG. 9 is a top view of one aspect of an absorbent article of the present invention.

FIG. 9 illustrates the article 10 where line C-C divides the shell 14 transversely (2) at the longitudinally extending (1) midpoint into substantially equal half portions. In desirable aspects, at least a portion of the anterior half 503 and/or the posterior half 505 of the first area 11 of the first side 15 of the shell 14 is designed or adapted to contact, attach or adhere to the wearer's skin. In one particular aspect, the first area 11 of the shell 14 is designed or adapted to contact a wearer's skin surrounding the vulva region of the female torso when the article 10 is applied to the wearer. By "designed or adapted to contact a wearer's skin surrounding the vulva region of the female torso", it is meant that the size and shape of the shell is such that the shell fits in the vulva region and optionally the surrounding pubic region and/or perinea regions and/or coccyx of the female torso. In one particular aspect, the anterior edge 20A of the shell is present in the pubic hair region above the vagina area of the female torso and the posterior edge 20B is present in the coccyx area of the female torso.

Generally, the shell 14 is desirably sized and shaped such that at least a portion of the first area 14 of the shell only contacts and attaches or adheres to the skin and/or hair surrounding and proximate to the vulva area and/or the pubic and/or perinea and/or coccyx regions of the wearer. Accordingly, in addition to contacting the skin in the vulva, pubic perinea and/or coccyx regions of the wearer, the first area 11 of the first side 15 of the shell 14 may also, or alternatively, contact and attach or adhere to any hair in which may be present in such regions.

In some aspects, the article is an absorbent article. Generally, the second area 12 of the shell 14 is the portion of the shell 14 onto which the absorbent structure 21 is attached to provide absorbency to the article. In some aspects of the present invention, the second area 12 of the shell 14 has an absorbent structure 21 contained therein or attached to the shell 14 in the second area to form the absorbent article 10. In additional aspects, the second area 12 of the shell 14 has an absorbent structure attachment means for connecting, hinging or changing out the absorbent structure 21 during use.

Figure 4:
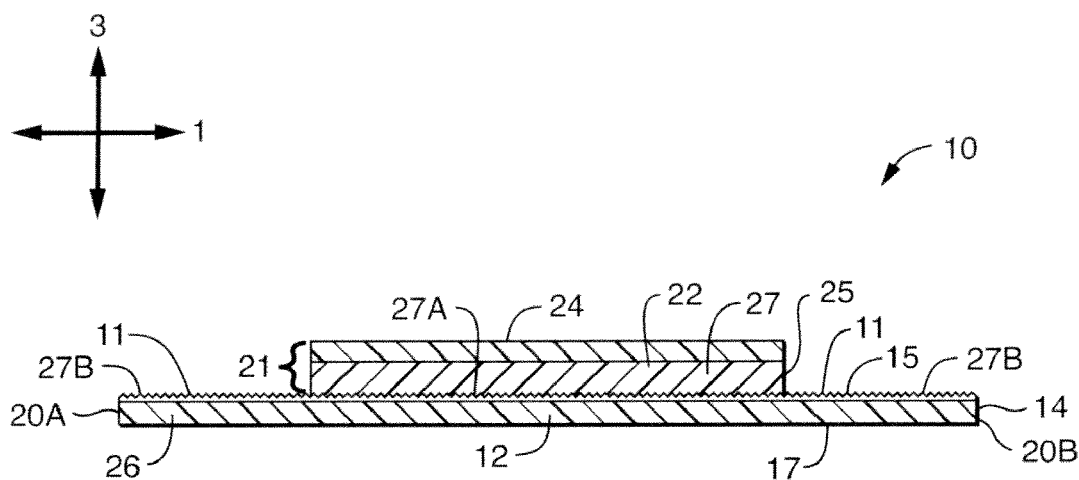
FIG. 4 is a longitudinal cross section view of one aspect of an absorbent article taken along line A-A of FIG. 1.

In some aspects, as seen in FIG. 4, the second area 12 can include both a separate absorbent structure 21 and an absorbent material 27A and/or 27B, such as a superabsorbent material for example, coated onto and/or integrated into the shell 14. In further aspects, the first area 11 of the shell 14 can also, or alternatively, at least partially include an absorbent material 27B coated onto and/or integrated into the shell. In other words, the absorbent material can be present in at least a portion of the first area 11. Other such variations or combinations of absorbent structures and absorbent materials with respect to the first area 11 and the second area 12 will be apparent to those skilled in the art. In aspects which include the presence of an absorbent structure 21, such structure can be attached to the shell 14 using methods well known in the art, such as adhesives, discussed in more detail below.

To gain a better understanding of the vulva region and surrounding regions of the female body, a general description of the anatomical structures can be found in *The Illustrated Running Press Edition of the American Classic Gray's Anatomy* (1974) by Henry Gray and *Structure and Function in Man* (1974) by Stanley W. Jacob, M.D., F.A.C.S. and relevant portions are included herein by reference. The general form can be found in *Anatomy for an Artist: Elements of Form* by Eliot Goldfinger and relevant portions are included herein by reference. The general description of the pubic hair covering these regions can be found in *Woman's Body: A Manual for Life* and relevant portions are included herein by reference.

The female anatomical structures to be described include the leg and the lower torso. The external anatomical structures of the lower torso include the gluteal region and the perineum region. The gluteal region includes the buttocks and the anus. The anatomical structure involved on the leg is the medial surface of the upper thigh.

The gluteal region includes generally the buttocks and anus and is typically bound in front by the line of the buttocks and the gluteal folds, in the back by the sacral triangle and the sides by lines extending through the greater trochanters. The shape of the gluteal region is roughly hemi-spherical and convex and is determined by a series of muscles, including the gluteus maximus and a series of fat pads including the posterior gluteal fat pad. The line of the buttocks separates the gluteal region and the perineum region.

The upper thigh region includes typically the right and left thigh and is typically bound on top by the thigh lines and the sides by the front and back of the leg. The thigh lines are two lines that are on either side of the labia and each of the lines runs along the line of the inguinal ligament to the gluteal folds and marks where the upper thigh meets the lower torso. The shape of the region is roughly a portion of a tapered cylinder and convex, and is shaped by a series of muscle groups including the gracilis, pectineus, adductor longus, adductor brevis, and adductor magnus and series of fat pads including the inner thigh fat pad.

The perineum region, which extends from the inferior outlet of the pelvis to the bony structure of the coccyx, is comprised of two divisions, the urogenital triangle and the anal division or obstetrical perineum. The region includes the external organs of reproduction; the mons pubis, labia majora and minora, clitoris, meatus urinarius and the opening to the vagina. The region is generally bound in front by the lower abdominal line, on the sides the thigh lines, and in the back the line of the buttocks. The abdominal line is a line that passes across the top of the pubis. The lines of the buttocks are lines that connect the thigh lines to the gluteal cleft. For convenience in describing the form and created spaces in the perineum region, this region will be subdivided into three regions including an anterior region including the mons pubis, a central region including the labia majora and minora, and posterior region. The anterior region is bound in front by the lower abdominal line, in back by anterior commissure, and on the sides by line of the labia. The central region is bound in front by the anterior commissure, in the back by the posterior commissure, and on the side by the line of the labia. The posterior region is bound in front by the line of the labia, in the back by the lines of the buttocks, and on the sides by the thigh line.

The vulva region includes the female external genitalia and generally includes the anterior and central regions of the perineum. The mons pubis [or veneris] is generally a rounded eminence in front of the symphysis pubis, formed by a collection of fatty tissue including the pubic fat pad beneath the integument and is generally covered with pubic hair. The labia majora are generally two prominent longitudinal cutaneous folds extending downward from the mons veneris to the anterior boundary of the perineum, and generally enclosing the common urinary-sexual opening. The space between the two folds is the labial cleft. Each labium has generally two surfaces, an outer, which is pigmented and covered generally with strong, crisp pubic hairs, and an inner within the labia cleft, which is smooth and is beset with large sebaceous follicles and is continuous with the genito-urinary mucous tract; between the two there is considerable quantity of areolar tissue, fat including the labia fat pad, and tissue besides vessels, meeting the anterior commissure. Posteriorly they are typically not joined, but generally appear to become lost in the neighboring integument, terminating close to, and nearly parallel with each other. Together with the connecting skin between them, they form the posterior commissure or posterior boundary of the vulval orifice. The interval between the posterior commissure and the anus constitutes the perineum region. The fourchette is the anterior edge of the perineum, and between it and the hymen is a depression, the fossa navicularis. The line of the labia separates the labia and the perineum region.

The labia minora are two small cutaneous folds, situated generally within the labia majora, and extending from the clitoris obliquely downward, outward, and backward on each side of the orifice of the vagina.

The form of the perineum, gluteal, and upper thigh regions combine to form a very intricate skin topography and spaces. The roughly two-hemispherical-like forms of the buttocks, the roughly tapered-cylinder-like form of the upper thigh, split-teardrop-like form of the vulvar region create intricate generally convex topography with intersections to form a series of recesses. The generally convex topography of the buttocks, the vulvar region, and upper thigh join to create spaces including two inner thigh grooves along two thigh lines, a depression in the posterior perineum region and a cleft extending through the labia and gluteal clefts. The grooves, depression, and cleft are like interconnected recesses in the topography. The central region general has lateral sides separated by a distal surface created by the labial cleft and includes the labial cleft.

Pubic hair generally cover some of these regions and fill in a portion of these recesses especially the labial cleft and the portion of the groove of the thigh parallel to the labial cleft to create a hair surface topography. The hair topography is the surface topography of an imaginary distal surface created by the hair. The depression of the perineum, thigh groove parallel to the gluteal cleft, and the gluteal cleft generally has little or no pubic hair. The skin topography combines with the hair topography to create an overall body topography.

This intricate space created by the intricate body form in this region of the body varies between women in both size and form, and varies with the position and movement of the women. Some of these variations are summarized in "Female genital appearance: 'normality' unfolds" by Jillian Lloyd et al., *BJOG: An International Journal of Obstetrics and Gynecology*, May 2005, Vol. 112, pp. 643-646 and is included herein by reference.

The shell 14 of the article 10 of the present invention may be prepared from a variety of materials. For example, the shell may include a layer constructed of any material which will provide the desired performance of the article. In some aspects, the shell material 26 can be operatively liquid impermeable, while in other aspects, the shell material can be operatively liquid permeable. In still other aspects, the shell material can include combinations of liquid permeable and liquid impermeable materials, such as to form regions in the x-, y- and/or z-direction, for example. In some particular aspects, the shell 14 comprises liquid permeable material in the first area 11 of the shell 14, and liquid impermeable material (or materials that are treated to be liquid impermeable) in the second area 12 of the shell 14.

Figure 5:
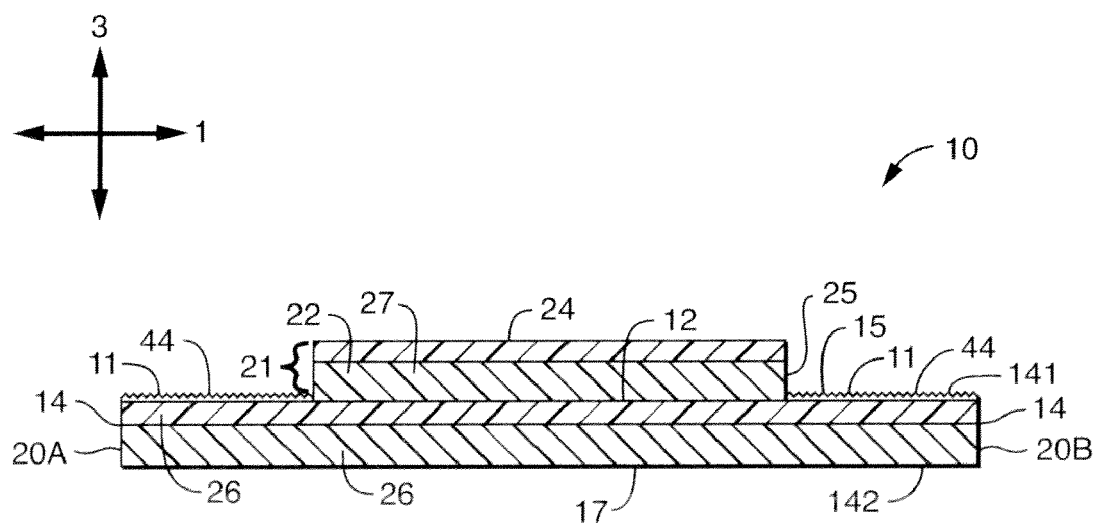
FIG. 5 is a longitudinal cross section view of one aspect of an absorbent article taken along line A-A of FIG. 1.

In general, the shell 14 can include a polymeric film, a nonwoven fabric, a foam or the like, as well as combinations or composites thereof. In some aspects, the shell 14 may include a laminate structure, such as a polymer film laminated to a woven or nonwoven fabric, for example, provided that it is disposable, as defined above. In this particular feature, the polymer film can be composed of polyethylene, polypropylene, polyester, silicone and the like, as well as combinations thereof. A laminate shell 14 structure is shown in FIG. 5, having an upper layer 141 and a lower layer 142, wherein the upper layer 141 is the body-facing side of the shell 14 and the lower layer 142 is the garment-facing side of the shell 14.

In some aspects, at least a portion of the first side 15 and/or the second side 17 of the shell 14 can be micro-embossed, textured, have a printed design, have a printed message, and/or may be at least partially colored. In one particular aspect, the shell is colored and/or printed to resemble a non-disposable undergarment.

In some aspects, the shell 14 can operatively permit a sufficient passage of air and moisture vapor out of the article 10, particularly out of the absorbent structure 21, while blocking the passage of bodily fluids, and/or odors often associated with bodily fluids, particularly in the second area 12. Accordingly, other non-limiting examples of a suitable shell material can include a breathable, microporous film, such as those described in, for example, U.S. Pat. No. 6,045,900 to Haffner et al., which is incorporated herein by reference in a manner that is consistent herewith. Still other shell materials include those that are extensible or elastically extensible. In some aspects, the shell material 26 can have portions that have different properties, for example, portions of the shell 14 can be elastic in one or more directions, portions that can be extensible in one or more direction, and/or portions that can be inelastic. In some desirable aspects, the shell material 26 is at least partially elastic to properly fit varying body shapes and changes in body shape during wear as a result of change in body position. Accordingly, the shell can have different areas of extensibility or elasticity to provide improved benefits. In some aspects, the shell has an anterior half 703 and a posterior half 705 (FIGS. 16 and 22) where the posterior half exhibits a higher extension relative to the anterior half when a stretching force of 454 grams is applied, as measured by the % Strain Differential Test. For example, in some aspects, the posterior half 703 exhibits at least a 5% greater extension, such as at least a 10% greater extension, or at least a 15% greater extension or more, as measured by the % Strain Differential Test.

Suitable shell materials can also include various types of foams, including, but not limited to, thermoplastic foams, high internal phase emulsion (HIPE) foams and inverse high internal phase emulsion (I-HIPE) foams, and other suitable polymeric foams, including, but not limited to, those disclosed in U.S. Pat. No. 7,053,131 to Ko et al., U.S. Pat. No. 7,358,282 to Krueger et al. and U.S. Publication No. US2006/0148917 to Radwanski et al., which are incorporated herein by reference in a manner that is consistent herewith. One such example of a suitable foam is a polyurethane foam with a negative Poisson ratio. Materials typically used as backsheet materials in conventional feminine pads can also be suitable. Examples of extensible backsheet materials are described in U.S. Pat. No. 5,611,790, issued Mar. 18, 1997, to Osborn, III et al., herein incorporated by reference in a manner that is consistent herewith. However, it should be understood that the shell 14 is not considered to be a backsheet of the absorbent structure 21 of the present invention. Rather, the shell 14 is considered to be a separate structure from the absorbent structure 21, regardless of whether or not the absorbent structure 21 includes a backsheet 23. Other materials that are inherently breathable, such as polyurethanes, may be used to form the shell 14.

In one particular aspect of the present invention, the shell 14 may be a laminate of a woven or nonwoven fabric with a silicone polymer, wherein the silicone polymer has adhesive properties. In this aspect, the second side 17 of the shell 14 can be the woven or nonwoven fabric and the first side 15 of the shell 14 can be the silicone polymer. One commercially available laminate is an OLEEVA FABRIC 1, available from Bio Med Sciences, Inc., having a place of business in Allentown, Pa., U.S.A. The OLEEVA fabric is a silicone sheeting having adhesive properties laminated to a fabric backing. In particular features of this aspect, the silicone sheeting can form the body-facing first side 15 of the shell material 26. Relating this particular structure to the Figures, in FIG. 5, the silicone polymer is the upper layer 141 of the shell 14 and the nonwoven or woven layer is the lower layer 142 of the shell.

Bicomponent films or other multi-component films can also be used as the shell material 26. In addition, in some aspects, woven and/or nonwoven fabrics which have been treated to render them operatively liquid-impermeable or liquid permeable can also be used as an effective shell material 26. Another suitable shell material 26 can include a closed-cell polyolefin foam, a polyurethane polymer material, a silicone polymer or other similar materials.

In some desirable aspects, silicone polymers having naturally occurring adhesive properties, or silicone polymers having a silicone adhesive layer applied thereto, can be used for the shell material. Such silicone polymers can allow the first area 11 of the shell 14 to adhere to the body of the wearer without the need of an additional adhesive. These materials may be laminated to another material, such that the other material is present on the second side 17 of the shell 14, which is the garment-facing side of the article 10, so that the adhesive nature of the silicone polymer does not adhere to the undergarments of the wearer. In another aspect of the present invention, the shell material 26 may be prepared from an interpenetrating polymer network of two or more polymers. Generally, one of the polymers of the interpenetrating polymer network may be a silicone material. Examples of interpenetrating polymer networks are described in U.S. Pat. No. 5,759,560, issued to Dillion, which is hereby incorporated by reference in a manner that is consistent herewith.

The shell material 26 should be selected such that the overall properties of the shell 14 allow the shell material to move with the skin of the wearer during normal use and normal movements by the wearer during use. By "normal movement by the wearer" it is meant any movement that normally occurs during use of the article, including, walking, running, sitting, laying, standing, kneeling, riding a bicycle, exercising, lifting, playing sports, getting into and out of an automobile, and other similar movements made by wearers when wearing the article. The shell 14 should not be too rigid, such that the shell detaches from the skin of the wearer during use, and the shell 14 should not be so flexible that the shell tends to twist and bunch during use. The shell 14 desirably has sufficient flexibility to conform to the skin of the wearer and become similar to an additional skin of the wearer. The shell 14 also desirably has the ability to remain attached to the body of the wearer under dry, moist or wet conditions.

Generally, the shell material 26 should have sufficient thickness to allow the shell 14 to mold to the body of the wearer, but not too thick such that the shell 14 becomes uncomfortable for the wearer to wear. In addition, the shell 14 should not be so thin that it ineffectively forms a seal with the skin of the wearer when applied to the wearer, or becomes detached from the skin of the wearer during use and normal movement of the wearer during use, or that it does not adequately conform to the shape and skin of the wearer at the point of attachment to the wearer. Depending on the material used for the shell 14, the typical thickness of the shell is between about 0.03 mm and about 5.0 mm, such as between about 0.1 mm and about 3.0 mm, or between about 0.25 mm and about 3.0 mm to provide improved benefits. Again, the actual thickness used is dependent on several factors including rigidity of the material, the flexibility of the material and the ability of the material to assume the shape of the skin of the wearer at the location of use, which is typically the vulva region of a wearer, but can extend through the coccyx region in some desirable aspects.

Generally, the second side 17 of the shell 14 forms at least a portion of the garment-facing side of the article 10 when worn by a wearer. In some aspects, the shell material 26 can be selected such that the second side 17 of the shell 14 will freely move against the undergarment or clothing of a wearer. One way to achieve this result is to construct the second side 17 of the shell 14 to have a fairly low coefficient of friction, preferably the same or lower coefficient of friction as the adjacent surface of a garment with which the shell comes in contact with, such as an undergarment or other clothing. This will allow the second side 17 of the shell 14 to freely move against the undergarment or other clothing worn by the wearer. In this particular aspect, if the second side 17 of the shell 14 does not freely move against the undergarment or other clothing worn by the wearer, the article 10 may catch on the undergarment or clothing, which can result in the article being prematurely and undesirably removed from the wearer, or may cause the article 10 to be shifted from its desired placement against the body of a wearer. However, in other aspects, it may be desirable that at least one or more portions of the second side 17 of the shell 14 have a coefficient of friction that is higher relative to the adjacent surface of a garment with which the shell comes in contact with. For example, as seen in FIG. 3, the shell 14 of the article of the present invention can be configured to have an anterior region 7, a posterior region 9 that is distal of the anterior region, and a central region 8 located between the anterior region and the posterior region. In this particular aspect, with respect to the adjacent surface of a garment with which the second side 17 of the shell 14 comes in contact with, at least a part of one of both distal end portions (i.e., anterior region 7 and/or posterior region 9 of the shell) can have a higher coefficient of friction, whereas, at least the central region 8 of the second side 17 of the shell 14 can have a coefficient of friction that is the same or less than that of the adjacent surface of the garment, as measured by the Coefficient of Friction Test.

In order to achieve the desired coefficient of friction on the second side 17 of the shell 14, the materials used to prepare the shell can be selected such that the second side 17 of the shell material 26 will inherently have the desired coefficient of friction. Alternatively, the second side 17 of the shell 14 may be treated with a coating composition, such as polytetrafluoroethylene containing coating, a silicone containing coating or other similar coating having low coefficient of friction properties, for example.

In some aspects, the shell 14 can be made from a laminate of two or more materials such that the first side 15 of the shell 14 is prepared from a material which meets the needed properties of the first side 15 (such as gentle to the skin and/or hair, for example), while the material selected for the second side 17 of the shell 14 meets the desired coefficient of friction such that the second side 17 will freely move against the undergarment or other clothing worn by a wearer. Accordingly, in some aspects, the shell 14 can be a unitary structure having desired surfaces, or regions, on the same surface of differing coefficients of friction.

The shell 14 of the article 10 may be flat or may have a three-dimensional shape. When the shell 14 is a generally flat shape, meaning that the shell does not have a third dimension other than thickness, the shell 14 is desirably constructed to be flexible enough such that the shell 14 can conform to the body of the wearer at the point of attachment. In addition to being flat, the overall shape of the shell 14 may be contoured in the z-direction. Such contour shape is one of many possible shapes that the shell 14 may have. Other shapes may be used without departing from the scope of the present invention. Generally, the shape selected should be such that the shell 14 and article 10 provide comfort and/or confidence to the wearer, while providing leakage protection to the wearer.

In general, the shell 14 may be any desired color and/or may be translucent. By "translucent" it is meant that the shell 14 has a minimum light transmittance of about 45% or more, such as about 60% or more, or 80% or more, such as in the range of about 60% to about 79%, as measured by as measured by the Light Transmittance Test. In addition, the shell 14 may have one or more of a various finish, such as matte finish, satin finish or a smooth finish, or combinations thereof, for example. The particular finish, color or translucency can be a matter of choice for the manufacturer of the article of the present invention. However, by providing a shell which is translucent may assist the wearer in placing the article 10 prior to or during use, since the wearer may be able to see where the article is placed compared to the genitalia of the wearer.

In desirable aspects, the article further comprises an absorbent structure and optionally an absorbent material to form an absorbent article 10. The absorbent structure 21 and optional absorbent material 27A and/or 27B (e.g., FIG. 4) are intended to absorb body exudates, including menstrual fluid, blood, urine, and/or other bodily fluids, such as sweat and vaginal discharges. In the case of an absorbent structure, the absorbent structure 21 has a longitudinal direction 1, a lateral direction 2, and a z-direction 3. The absorbent structure 21 may be a single layer or may be multiple layers. In some desirable aspects, as seen in FIGS. 4-7, the absorbent structure 21 has an absorbent core 22, and can optionally comprise additional layers, such as a generally liquid-permeable topsheet 24 and/or a generally liquid-impermeable backsheet 23. The absorbent core 22 may contain one or more layers of absorbent materials 27, such as fibrous materials and/or superabsorbent materials for example. That is, the absorbent core 22 may be a single layer or may be a multilayer structure. Each of the layers can contain similar materials or different materials. In some aspects, the article of the present invention is an absorbent article 10, where the materials that can be used to form the absorbent core 22 include those materials conventionally used in absorbent articles and includes materials, such as cellulose, wood pulp fluff, rayon, cotton, and meltblown polymers such as polyester, polypropylene or coform, for example. In one particular aspect, the absorbent structure 21 includes a coform that is a combination of meltblown polymers, such as polypropylene, and absorbent staple fibers, such as cellulose. In another particular aspect, the absorbent structure 21 includes a wood pulp fluff, since it is low in cost, relatively easy to form, and has good absorbency. In some aspects, the absorbent core 22 can comprise a foam, including but not limited to, a polyurethane foam, a thermoplastic foam, a high internal phase emulsion (HIPE) foam, an inverse high internal phase emulsion (IHIPE) foam, and the like, and combinations thereof.

The absorbent core 22 can also be formed from a composite comprised of a hydrophilic material which may be formed from various natural or synthetic fibers, wood pulp fibers, regenerated cellulose or cotton fibers, or a blend of pulp and other fibers. One particular example of a material which may be used as the absorbent core is an airlaid material. The absorbent core 22 may have other properties including extensibility and elastic extensibility, which will allow the absorbent core to be extended or fit to a particular wearer. One example of extensible absorbent cores is described in U.S. Pat. No. 5,611,790 to Osborn, III et al., herein incorporated by reference in a manner that is consistent herewith. One example of elastically extensible absorbent cores is described in U.S. Pat. No. 6,362,389 to McDowall, herein incorporated by reference in a manner that is consistent herewith.

As referenced above, in some aspects, the absorbent core 22 also includes a superabsorbent material, in addition to or in place of fibrous materials which increases the ability of the absorbent core to absorb a large amount of fluid in relation to its own weight. The superabsorbent materials can be inserted as particles or in sheet or film-form, which may be continuous or discontinuous, and which may or may not be in the form of a pattern. In some aspects, the superabsorbent polymer may be applied as a liquid. The superabsorbent material may optionally be biodegradable or bipolar. The hydrogel-forming polymeric absorbent material may be formed from organic hydrogel-forming polymeric material, which may include natural material such as agar, pectin, and guar gum; modified natural materials such as carboxymethyl cellulose, carboxyethyl cellulose, and hydroxypropyl cellulose. The hydrogel-forming polymeric absorbent material may also be formed from synthetic hydrogel-forming polymers. Synthetic hydrogel-forming polymers include, for example, alkali metal salts of polyacrylic acid, polyacrylamides, polyvinyl alcohol, ethylene maleic anhydride copolymers, polyvinyl ethers, polyvinyl morpholinone, polymers and copolymers of vinyl sulfonic acid, polyacrylates, polyacrylamides, polyvinyl pyridine, and the like. Other suitable hydrogel-forming polymers include hydrolyzed acrylonitrile grafted starch, acrylic acid grafted starch, and isobutylene maleic anhydride copolymers and mixtures thereof. The hydrogel-forming polymers may be lightly crosslinked to render the material substantially water insoluble. Crosslinking may, for example, be by irradiation or covalent, ionic, Van der Waals, or hydrogen bonding. Hydroxyfunctional polymers have been found to be good superabsorbents for sanitary napkins. Such superabsorbents are commercially available from BASF and Evonik Stockhausen, Inc., among others. Other types of superabsorbent materials known to those skilled in the art can also be used.

Figure 6:
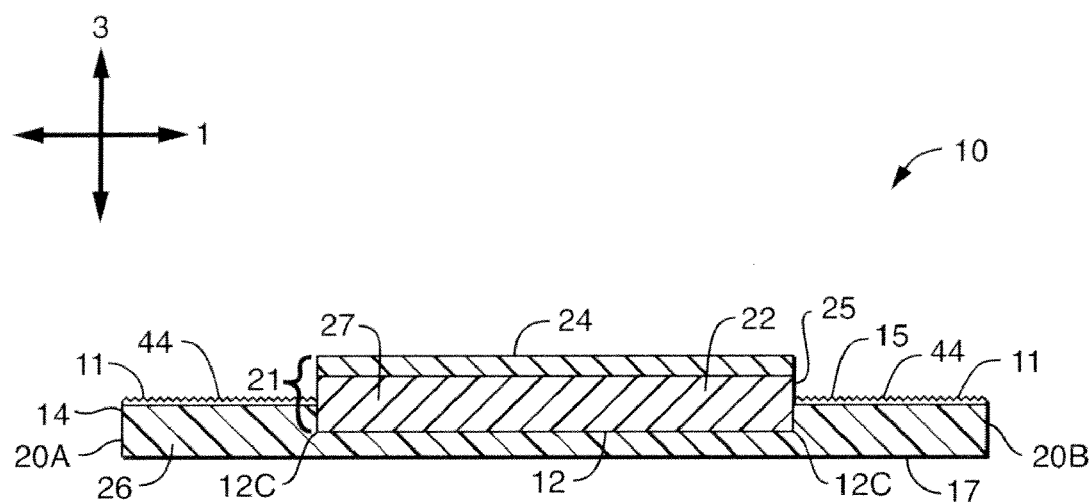
FIG. 6 is a longitudinal cross section view of one aspect of an absorbent article taken along line A-A of FIG. 1.

Generally, the absorbent core 22 will be positioned adjacent the shell 14, as is shown in FIGS. 4-7, for example. By "adjacent to the shell", it is meant that the absorbent core 22 is directly in contact with the shell or may be separated by one or two additional layers and/or an attachment means, such as a bonding agent, such as pressure sensitive adhesive for example. In addition, the absorbent core 22 may be recessed into the shell 14 as is shown in FIG. 6.

As referenced above, in addition to the absorbent core 22, the absorbent structure 21 may include other additional layers which aid the absorbent core 22 in capturing and holding the bodily fluid into the absorbent core 22. These other optional layers, including a topsheet 24 and/or backsheet 23, when present, in combination with the absorbent core 22, form the absorbent structure 21 of the article 10. There may be a single layer or multiple layers in addition to the absorbent core in the absorbent structure 21. Alternatively, the absorbent structure 21 may be a single layer, which is generally the absorbent core 22.

Figure 10:
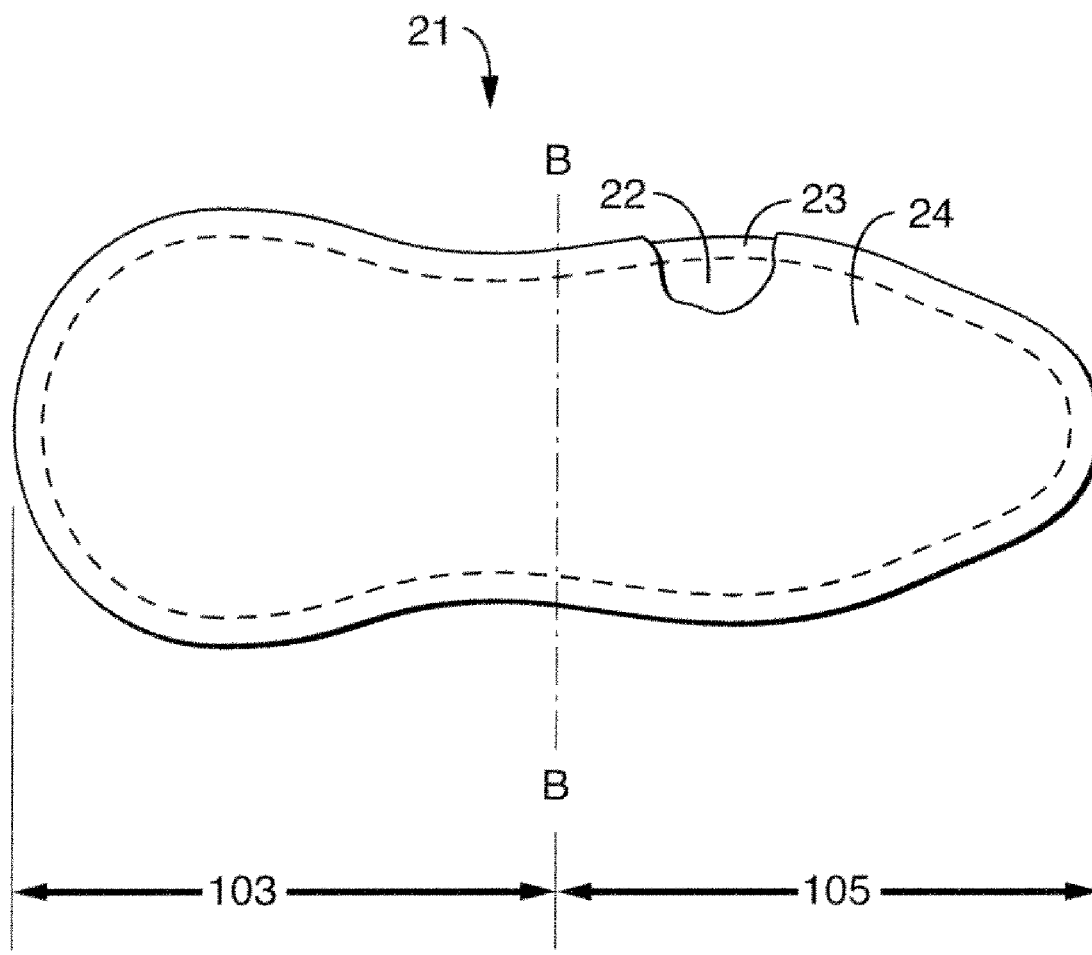
FIG. 10 is a top view of one aspect of an absorbent structure of the present invention.

For purposes of reference, the absorbent structure can be divided in half, resulting in an anterior half 103 and a posterior half 105. This is illustrated in FIG. 2 where line B-B divides the absorbent structure 21 transversely (2) at the longitudinally extending (1) midpoint into substantially equal portions. In some aspects, the absorbent structure 21 has approximately the same area in the anterior half 103 as in the posterior half 105, whereas in other aspects, it may be desirable to have more area in either the anterior half 103 or in the posterior half 105. For example, FIG. 10 shows an absorbent structure 21 that has more area in the anterior half 103 than in the posterior half 105, which can provide improved coverage, absorbency, and fit in some aspects.

As shown in FIGS. 4-6, one particular example of an additional layer which may be used in addition to the absorbent core 22 in the absorbent structure 21 is a body-side liner (i.e., a topsheet) 24, which is generally a liquid permeable material, which allows bodily fluids to pass through the topsheet into the absorbent core. It is noted that the terms "body-side liner" and "topsheet" may be used interchangeably. The topsheet 24 can also provide the wearer with a dry feeling by separating the absorbent core 22 from the body of the wearer. That is, the topsheet 24 is placed between the absorbent core 22 and the body of the wearer such that the absorbent core 22 is between the topsheet 24 and the shell 14.

In the present invention, generally the topsheet 24 will only extend to the edge 25 of the absorbent core, as is shown in FIGS. 4-6. However, in some aspects, the topsheet 24 may extend beyond the edge 25 of the absorbent core 22 and may optionally be attached to the first side 15 of the shell 14. Generally, if the topsheet 24 extends beyond the absorbent core 22, any portions of the topsheet 24 that are attached to the shell 14 will be attached to the first side 15 of the shell 14. Also, if the topsheet 24 extends beyond the absorbent core 22, the topsheet 24 will generally not cover the entire first area 11 of the first side 15 of the shell 14.

Optionally, the topsheet 24 may be formed from one or more materials. The topsheet 24 should be able to manage different body excretions depending on the type of product. In feminine care products, often the topsheet 24 must be able to handle complex fluids, such as menses and mucin for example, as well as urine. In the present invention, the topsheet 24 may include a layer constructed of any operative material, and may be a composite material. For example, the topsheet can include a woven fabric, a nonwoven fabric, a polymer film, a film-nonwoven fabric laminate, and the like, as well as combinations thereof. Examples of a nonwoven fabric useable in the topsheet 24 include, for example, an airlaid nonwoven web, a spunbond nonwoven web, a meltblown nonwoven web, a bonded-carded web, a hydroentangled nonwoven web, a spunlace web and the like, as well as combinations thereof. Other more particular examples of suitable materials for constructing the topsheet 24 can include rayon, bonded-carded webs of polyester, polypropylene, polyethylene, nylon, or other heat-bondable fibers, finely perforated film webs, net-like materials, and the like, as well as combinations thereof. These webs can be prepared from polymeric materials such as, for example, polyolefins, such as polypropylene and polyethylene and copolymers thereof, polyesters in general including aliphatic esters such as polylactic acid, nylon or any other heat-bondable materials. When the body-side liner is a film or a film laminate, the film should be apertured or otherwise be made to allow fluids to flow through the body-side liner to the absorbent core.

Other examples of suitable materials for the topsheet 24 are composite materials of a polymer and a nonwoven fabric material. The composite materials are typically in the form of integral sheets generally formed by the extrusion of a polymer onto a nonwoven web, such as a spunbond material. In some aspects, the topsheet layer 24 can be configured to be operatively liquid-permeable with regard to the liquids that the article is intended to absorb or otherwise handle. The operative liquid-permeability may, for example, be provided by a plurality of pores, perforations, apertures or other openings, as well as combinations thereof, which are present or formed in the liner or body contacting layer. The apertures or other openings can help increase the rate at which bodily liquids can move through the thickness of the liner or body contacting layer and penetrate into the other components of the article (e.g. into the absorbent core 22). The selected arrangement of liquid permeability is desirably present at least on an operative portion of the topsheet 24 that is appointed for placement on the body-side of the article. The topsheet 24 can provide comfort and conformability, and can function to direct bodily exudates away from the body and toward the absorbent core 22. The topsheet 24 can be configured to retain little or no liquid in its structure, and can be configured to provide a relatively comfortable and non-irritating surface next to the body tissues of a wearer. In the present invention, the topsheet 24 or other body-facing surface of the absorbent structure 21 may be embossed, printed or otherwise imparted with a pattern or color.

In some aspects, additional layers or substrates, including for example, a liquid acquisition and/or distribution layer, also referred to as a surge or transfer layer, and an optional tissue layer are also incorporated into the absorbent structure 21 of the absorbent structure 21, for example, between the topsheet 24 and the absorbent core 22. A distribution layer, if present, may be shorter than the absorbent core or have the same length as the absorbent core 22. The distribution layer serves to temporarily hold an insulting fluid to allow the absorbent core sufficient time to absorb the fluid, especially when a superabsorbent material is present.

In other aspects, the absorbent core, optional transfer layer and other optional components, such as tissue layers, may be free floating (unattached) between the shell 14 and the topsheet 24, and are secured along only the peripheral edges thereof. Alternatively, the absorbent core 22, transfer layer, if present, and any other layer or component, if present, may be attached to one or both of the shell 14 and topsheet 24 and/or to each other.

In aspects wherein a liquid-impermeable backsheet is present (e.g., FIG. 7), the backsheet 23 will typically be located on the garment-facing side of the absorbent structure 21, such that the absorbent core is located between the backsheet 23 and the shell 14. The backsheet 23 may be prepared from a variety of materials which will function to provide desired properties. For example, the backsheet 23 may include a layer constructed of any operative material, and may have a selected level of liquid-permeability or liquid-impermeability, as desired. In some particular configurations, the backsheet 23 may be configured to provide an operatively liquid-impermeable backsheet structure. The backsheet 23 may, for example, include a polymeric film, a woven fabric, a nonwoven fabric, and the like, as well as combinations or composites thereof. For example, the backsheet 23 may include a polymer film laminated to a woven or nonwoven fabric. In a particular feature, the polymer film can be composed of polyethylene, polypropylene, polyester and the like, as well as combinations thereof. Additionally, the polymer film may be micro-embossed. Desirably, the backsheet 23 can operatively permit a sufficient passage of air and/or moisture vapor out of the article, particularly out of the absorbent core 22, while blocking the passage of bodily liquids. An example of a suitable backsheet material can include a breathable, microporous film, such as a HANJIN Breathable Backsheet available from Hanjin Printing, Hanjin P&C Company Limited, a business having offices located in Sahvon-li. Jungan-mvu.Kongiu-City, Chung cheong nam-do, Republic of South Korea. This backsheet material is a breathable film, which is dimple embossed and contains 47.78% calcium carbonate, 2.22% TiO2, and 50% polyethylene.

In a particular feature, the polymer film can have a minimum thickness of no less than about 0.025 mm, and in another feature, the polymer film can have a maximum thickness of no greater than about 0.13 mm. Bicomponent films or other multi-component films can also be used, as well as woven and/or nonwoven fabrics which have been treated to render them operatively liquid-impermeable. Another suitable backsheet material can include a closed-cell polyolefin foam. For example, closed-cell polyethylene foam may be employed. Still another example of a backsheet material would be a material that is similar to a polyethylene film which is used on commercially sold KOTEX brand pantiliners, and is obtainable from Pliant Corporation, a business having offices located in Schaumburg, Ill., U.S.A.

The absorbent structure 21 is generally attached to the first side 15 of the shell 14 in the second area 12 of the shell. The attachment may be in a permanent manner, meaning that the absorbent structure 21 is generally intended not to be removable by the wearer of the article 10. Alternatively, the absorbent structure 21 may be constructed to be removable by the wearer, meaning that a portion (i.e., hinged), or the entire, absorbent structure 21 may be removed by the user, and in some aspects may be replaced with another absorbent structure 21 by the wearer of the article 10, or be replaced with nothing at all. In still other aspects, a portion of the absorbent structure 21 may be permanently attached, while another portion of the absorbent structure 21 may be refastenably attached. By "refastenably attached" it is meant that the attachment is releasably attached (i.e., is intended to be removed by the wearer) and is configured to re-attach to the same or a different absorbent structure. In some aspects, when the absorbent structure 21 is attached to the shell 14 in a permanent manner, meaning that the absorbent structure is not intended to be removed by the wearer, various bonding means can be used, such as a construction adhesive for example. Examples of useable construction adhesives include any adhesive which will effectively hold the absorbent structure 21 in place, so as not to be separated from the shell 14. Commercially available construction adhesives usable in the present invention include, for example, REX-TAC adhesives available from Huntsman Polymers, having a place of business in Houston, Tex., U.S.A., as well as adhesives available from Bostik Findley, Inc, having a place of business in Wauwatosa, Wis., U.S.A. Other means may be used to hold the absorbent structure 21 to the shell 14 including bonding techniques known in the art, including, but not limited to, adhesive bonds, cohesive bonds, thermal bonds, ultrasonic bonds, embossing, crimping, entangling, fusing, hook and loop, or the like, and combinations thereof.

When the absorbent structure 21 is removably (refastenably) attached, the absorbent structure 21 is held in place on the shell 14 by a means which will allow the wearer to remove the absorbent structure 21. One such means of holding the absorbent structure 21 is by using a pressure sensitive adhesive. Suitable pressure sensitive adhesives include, but are not limited to, any commercially available pressure sensitive adhesive. Examples of suitable pressure sensitive adhesives suitable to removably hold the absorbent structure 21 in place on the shell 14 include pressure sensitive adhesives available from National Starch, having a place of business in Bridgewater, N.J., U.S.A. By providing an absorbent structure 21 which is removable, the shell 14 may be reused several times without the need to again replace the shell 14 when the absorbent structure 21 needs to be replaced. Also, by having a removable absorbent structure 21, the absorbent structure 21 can be selected by the wearer prior to use. This would allow the wearer to select an appropriate level of protection for a given day or allow the wearer to select a size or shape of the absorbent structure 21 which the wearer finds to be more comfortable or desirable. Other removable attachment means include, but are not limited to, hook-and-loop, buttons, snaps, nanofabricated adhesives, and the like, or combinations thereof.

Another advantage of having an absorbent structure 21 which is at least partially removable is that the wearer may be able to perform normal bodily functions, such as urination, without replacement of the entire article 10. By having an absorbent structure 21 that is at least partially removable, a wearer could remove the absorbent structure 21, urinate and return or replace the absorbent structure 21 only. This would alleviate the need for a wearer to replace the entire article 10 in order to perform bodily functions.

Figure 8:
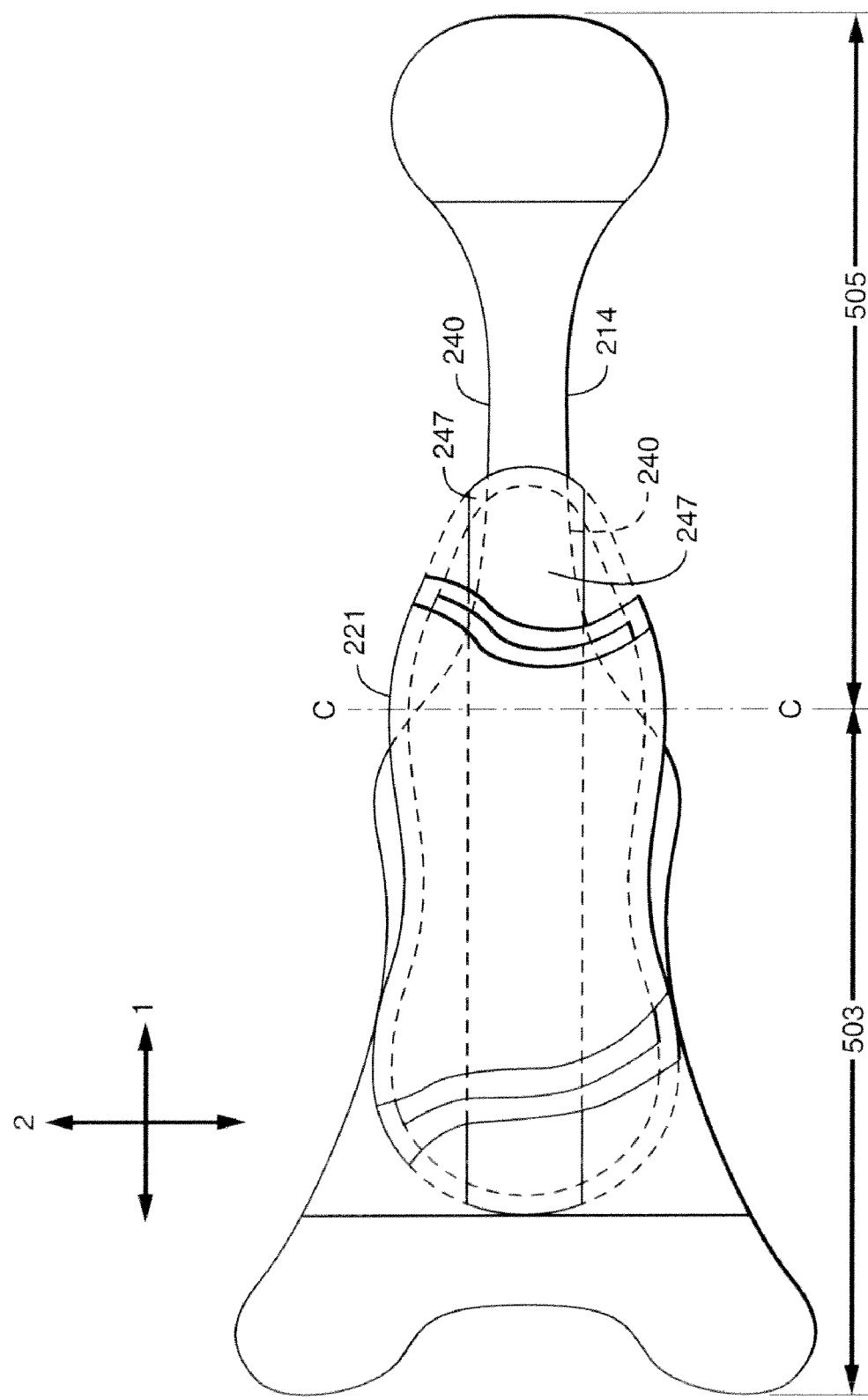
FIG. 8 is a top view of a comparative absorbent article.

FIG. 8 illustrates a typical absorbent article that is not specifically designed for use as the present invention. In the illustrated embodiment, the absorbent structure 221 is adhered to a shell 214 primarily throughout its entire length with attachment means 247 that limits extension in the posterior half 705 of shell 214. In contrast, it is desirable in the present invention to have stretch in the posterior half 705 of the shell 14 after application to provide improved benefits. In some aspects, it is also, or alternatively, desirable in the present invention for the absorbent structure 21 to become detached from the shell 14 in the posterior half 705 of the shell 14 allowing shell 14 to expand to meet the fit requirements as a result of changing body positions. Another disadvantage illustrated in this specific example in FIG. 8 is that the absorbent article attachment adhesive 247 extends past the peripheral edge 240 of shell 214. The exposed adhesive 247 could cause discomfort for the wearer of the article.

Figure 15:
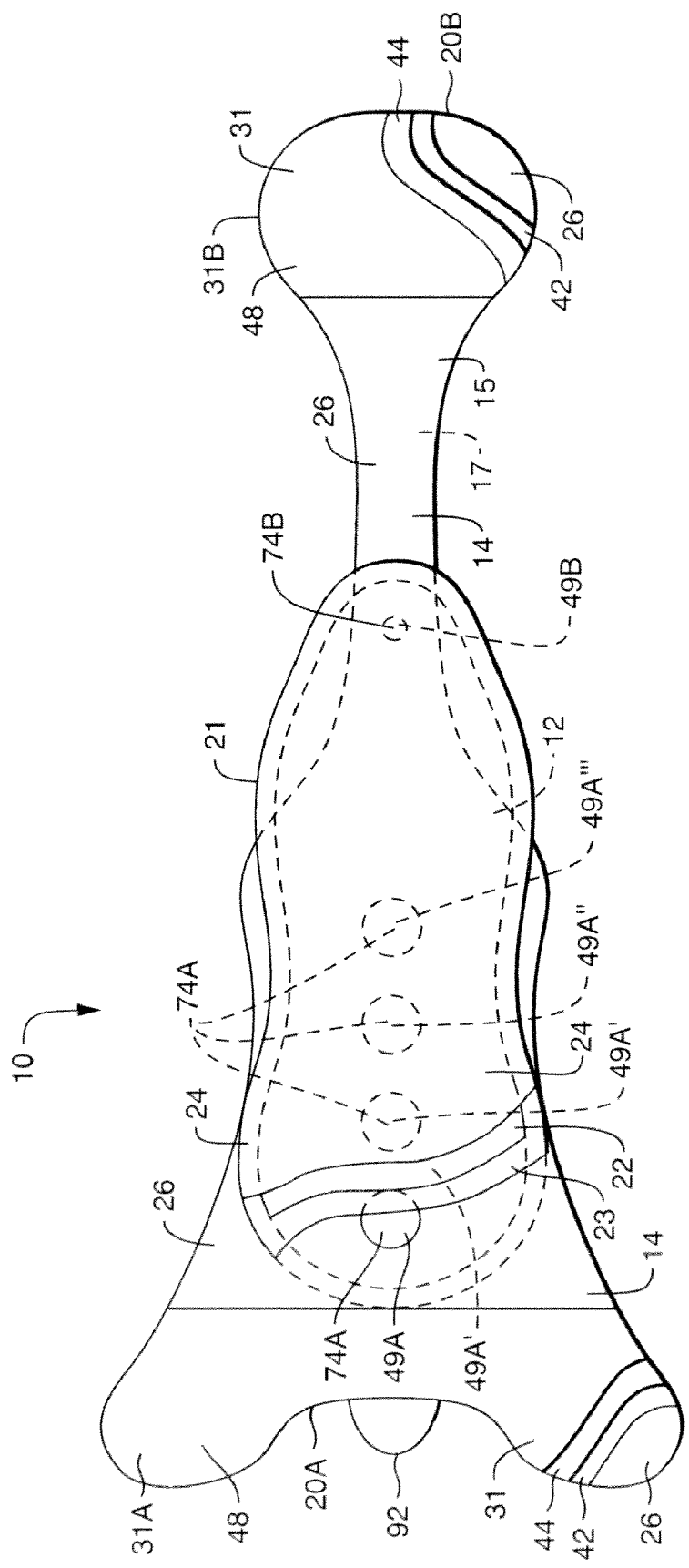
FIG. 15 is a top view of one aspect of an absorbent article of the present invention.
Figure 20:
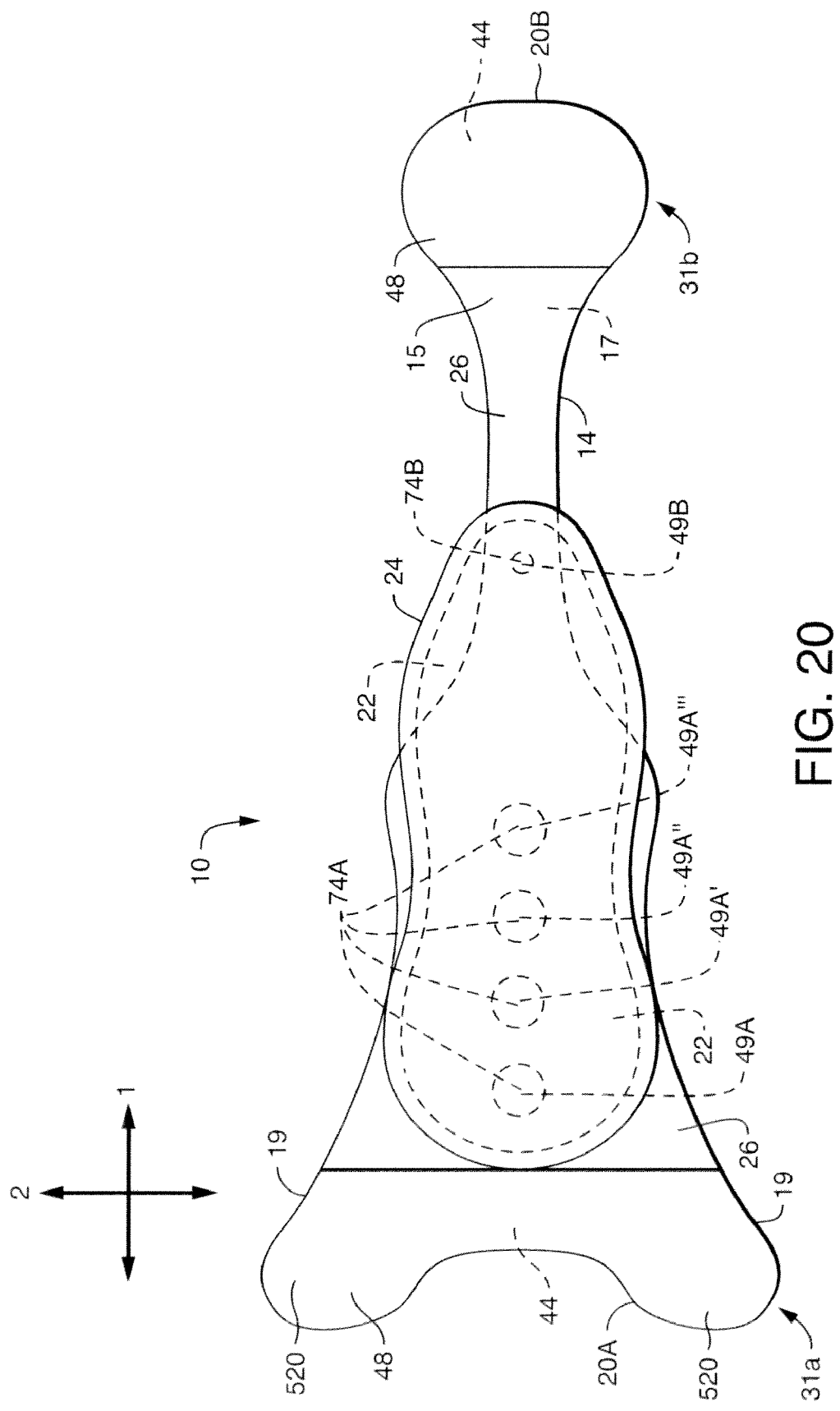
FIG. 20 is a top view of one aspect of an absorbent article of the present invention having spot bonds.

FIGS. 9,15,16 and 20 illustrate a desirable aspect of the invention where the absorbent structure 21 is configured such that it is attached to shell 14 in the anterior half 703 of the shell 14 with attachment means 74A, and in the posterior half 705 of the shell 14 with attachment means 74B to provide a snug fit with minimal gaps for a wide range of consumers over the entire range of movement. In some desirable aspects, the anterior attachment 74A is a permanent absorbent structure attachment, while posterior attachment 74B is a refastenable absorbent structure attachment, which is releasable (refastenable) (i.e., not permanent). The refastenable absorbent structure attachment 74B in the posterior half 705 is designed to remain attached during initial donning until sufficient force is applied by the consumer such that attachment 74B is severed. Preferably, the force to break refastenable absorbent structure attachment 74B is less than the donning force required to snug the product. In a particular aspect of this invention, the force to sever the refastenable absorbent structure attachment 74B is less than the knee point of shell 14. In some aspects, the force to sever the refastenable absorbent structure attachment 74B is less than the shear force to sever the permanent absorbent structure attachment 74A. When the posterior refastenable absorbent structure attachment 74B is severed, the posterior half 705 of the shell 14 is free to elongate to meet fit requirements as a result of changing body positions. In one particular aspect, the posterior half 705 of the body adhering article 10 will exhibit greater strain than the anterior half 703 when stress is applied to the entire body adhering article 10. Such a configuration (i.e., an anterior attachment means 74A and a separate posterior attachment means 74B) can allow the absorbent structure 21 to be partially free-floating with respect to the shell 14 (significantly more than the comparative embodiment illustrated in FIG. 8), allowing the article to better conform to the wearer during movement and various changes in position of the wearer. In some particularly desirable aspects, the anterior absorbent structure attachment means 74A and separate posterior absorbent structure attachment means 74B are in the form of a spot bond 49A and 49B, respectively, such as seen in FIG. 9. As used herein, the term "spot bond" refers to a bond point for attaching the article 21 to the shell 14, and each spot bond having an area in the range of about 5 mm$^2$ to about 200 mm$^2$. The spot bonds 49A, 49B can provide additional ability for the absorbent structure 21 to be at least partially free-floating in both the x- and/or y-position and/or z-direction to better conform to the wearer during movement and various changes in position of the wearer. In some aspects, the spot bonds can be ideal when the absorbent structure is removable, such as when the spot bond is in the form of a refastenable attachment means, including, but not limited to, a pressure sensitive adhesive, a hook-and-loop material, nanofabricated adhesive, buttons, snaps, and the like, and combinations thereof. In some aspects, multiple spot bonds can be present as the anterior absorbent structure attachment means 74A, posterior absorbent structure attachment means 74B, or both. In further aspects, the spot bonds 49A,49B can be placed in particular locations to provide improved benefits, such as improved fit and contour of the article during movement of the wearer, such as seen in FIGS. 9, 15 and 20.

Figure 21:
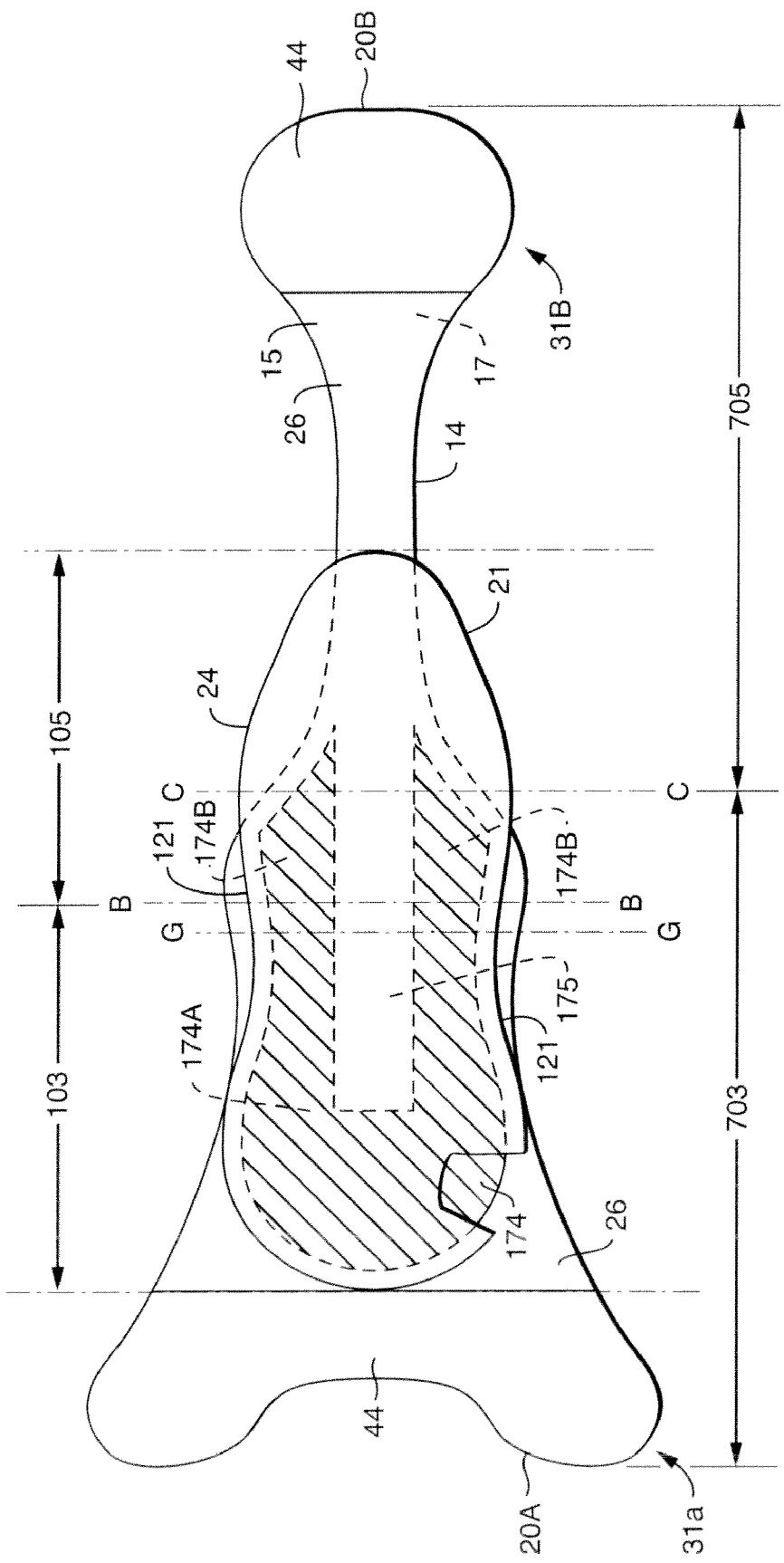
FIG. 21 is a top view of one aspect of an absorbent article of the present invention having an alternate absorbent structure attachment means.

In another aspect, as shown in FIG. 21, the absorbent structure 21 is configured such that it is attached to the shell 14 in the anterior half 703 and in the posterior half 705 of the shell 14 with attachment means 174 to provide a snug fit with minimal gaps for a wide range of consumers over the entire range of movement. The attachment means 174 is generally U-shaped and can be present in both the anterior half 103 of the absorbent structure 21 and in the posterior half 105 of the absorbent structure 21. It is understood that a generally U-shaped attachment means can also include other operative shapes, such as V-shaped, or variations thereof, without departing from the scope of the invention, provided that space 175 is present. In some aspects, the absorbent structure attachment means 174 is a permanent attachment means. In other aspects, the absorbent structure attachment means 174 is a refastenable attachment means. In some aspects, the absorbent structure attachment means 174 is configured to have an anterior portion 174A and a posterior portion 174B, as denoted by line G-G. In this aspect, the anterior portion of the attachment means 174A can be a permanent absorbent structure attachment, while the posterior portion of the attachment means 174B can be a refastenable absorbent structure attachment, which is releasable (i.e., not permanent). In this illustrated embodiment of FIG. 21, the refastenable absorbent structure attachment 174B is designed to remain attached during initial donning until sufficient force is applied by the consumer such that attachment 174B is severed. Preferably, the force to break the refastenable absorbent structure attachment 174B is less than the donning force required to snug the product. In a particular aspect of this invention, the force to sever the refastenable absorbent structure attachment 174B is less than the knee point of shell 14. In some aspects, the force to sever the refastenable absorbent structure attachment 174B is less than the shear force to sever the permanent absorbent structure attachment 174A. When the posterior refastenable absorbent structure attachment 174B is severed, the posterior half 705 of the shell 14 is free to elongate to meet fit requirements as a result of changing body positions. In one particular aspect, the posterior half 505 of the body adhering article 10 will exhibit greater strain than the anterior half 503 when stress is applied to the entire disposable body adhering article 10. Such a configuration (i.e., an anterior attachment means 174A and a posterior attachment means 174B) can allow the absorbent structure 21 to be partially free-floating in the non-adhesive portion 175 with respect to the shell 14 (significantly more than the comparative embodiment illustrated in FIG. 8) while providing secure attachment at the peripheral edges 121 of the absorbent structure 21, thus allowing the article to better conform to the wearer during movement and various changes in position of the wearer. In some aspects, the anterior attachment means 174A and posterior attachment means 174B can be ideal when the absorbent structure 21 is removable, such as when the posterior attachment means 174B is in the form of a refastenable attachment means, including, but not limited to, a pressure sensitive adhesive, a hook-and-loop material, nanofabricated adhesive, and the like, and combinations thereof.

To aid a wearer in replacing the absorbent structure 21, an absorbent structure placement aid may be present on the shell 14 and/or the absorbent structure 21. Suitable absorbent structure placement aids include the use of color, tactile indicators or any other means that would assist the wearer in replacing a removed absorbent structure.

As stated above, the absorbent structure 21, when present, is located in the second area 12 of the shell 14 and on the first side 15 of the shell 14. The size and shape of the absorbent structure 21 may be varied depending on the intended use of the article and will be discussed in more detail below.

In some aspects, the absorbent structure 21 can be a relatively flat structure, as shown in FIG. 10. Alternatively, the absorbent structure can have a three-dimensional shape other than a relatively flat shape, such as shown in FIG. 1. The absorbent structure can have an anatomically correct shape such that the absorbent structure fits within the labia of the wearer. Anatomically correct shapes of absorbent structures are generally known to those skilled in the art and are generally found in the interlabial art field. In some aspects, the absorbent structure may be designed to be partially or fully interlabial. Alternatively, a three-dimensional shaped absorbent structure 21 may also be used in the article 10 which is designed to not fit within the labia majora of the wearer. Accordingly, in some aspects, the absorbent structure 21 is positioned completely outside the labia during use.

The size, location and shape of the absorbent structure 21 may also be selected for an intended use. For example, in an overnight use, the absorbent structure 21 may be located further back on the wearer towards the perinea region of the wearer. In an overnight use, the absorbent structure may be larger than in a product intended for daytime use. In a daytime use, the absorbent structure will generally be centrally located in the vulva region.

In some aspects of the present invention, absorbent material 27A, 27B is contained within the shell material. For example, as seen in FIG. 4, the absorbent material 27A and/or 27B can be attached to or be an integral part of the shell 14. One way to achieve an integral absorbent structure is to have a shell 14 which is prepared from a material which is a laminate of two or more materials. The first side 15 of the shell 14 contains an absorbent material within the body-facing side of the laminate. For example, superabsorbent particles or materials may be incorporated into the material making up the body-facing layer of the shell 14. Another way is to place a coating of absorbent material onto the first area 11, the second area 12, or both, of the shell material 26. In some aspects, the absorbent material 27A,27B can be a coating containing superabsorbent particles, a superabsorbent sheet or film, or a liquid superabsorbent material. Such a coating can be continuous or discontinuous. It is understood that other absorbent materials (i.e., other than superabsorbent materials), may be used in place of, or in addition to, the superabsorbent materials.

Figure 7:
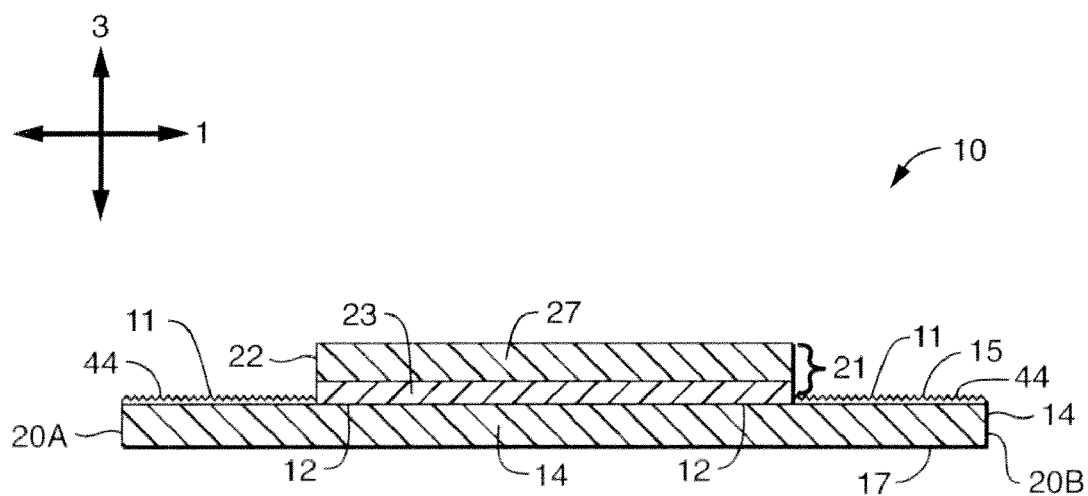
FIG. 7 is a longitudinal cross section view of one aspect of an absorbent article taken along line A-A of FIG. 1.

In some aspects, the entire absorbent structure 21 may be located over the second area 12 of the shell 14, meaning that the shell 14 material is located beneath the absorbent structure 21 and covers the entire bottom surface of the absorbent structure. In other aspects, the absorbent structure 21 is positioned over the shell 14, such that only a portion of the absorbent structure 21 is in contact with the shell 14, such as shown in FIGS. 1-3. More particularly, FIGS. 1-3 show an aspect where portions of the absorbent structure 21 extend past the peripheral edges 114 of the shell 14. As can be seen, only a portion of the absorbent structure 21 is positioned over the shell 14. As with the other aspects of the present invention, the portion of the first side 15 of the shell 14 in which the absorbent structure 21 is attached is the second area 12 of the shell 14. The second side 17 of the shell 14 is the side of the article which faces the wearer during use. By having a disposable personal care article with the structure shown in FIG. 1 where at least a portion of the absorbent structure 21 extends beyond the peripheral edges 114 of the shell 14, it may be beneficial for the absorbent structure to include a backsheet 23, such as shown in FIGS. 7 and 10. The backsheet 23 can then serve to provide liquid impermeability to the absorbent structure 21, such that any fluids entering the absorbent core 22 will not flow through the core to the clothing of a wearer. This is particularly desirable if the shell does not provide liquid-impermeable properties.

As referenced above, at least a portion of the first area 11 of the shell 14 serves to either directly or indirectly attach the article 10 to the body of a wearer. Stated another way, the shell 14 is the body attachment member and at least a portion of the first area 11 is the portion of the shell 14 which is attached to the body of the wearer. Depending on the material selected for the shell, the shell 14 may actively attach to the body of the wearer using electrostatic means, suction means, body adhesive means, frictional means, nanofabricated attachment means and the like, and combinations thereof, to attach the article to the body of a wearer. Electrostatic means can be used by selecting the shell material 26 to be a material which has an affinity for the body of a wearer, such that the shell material "clings" to the body of the wearer. Examples of such materials include ethylene vinyl acetate, low density polyethylene and other similar materials known to those skilled in the art. Suction means may be achieved by shaping the shell to conform to the body of the wearer, much like a contact lens fits to the eye. Generally, suction means can be achieved by forming the shell 14 into a three-dimensional shape. Frictional means can be used by selecting a material or modifying a material to have a desired coefficient of friction to prevent slippage or detachment, such as for a shell member that provides for attachment within the gluteal groove. Nanofabricated attachment means include those described in U.S. Patent Publication 2005/0148984 to Lindsay et al., which is incorporated herein by reference in a manner that is consistent herewith.

A further desirable means to achieve body attachment is to place a body adhesive in at least a portion of the first area 11 of the shell 14. For example, as shown in FIGS. 11-14, a body adhesive 44 can be positioned on the first area 11 of the first side 15 of the shell 14. The body adhesive 44 contacts the skin and/or hair, if present, in the vulva region and optionally the pubic region and/or the perinea region and/or the gluteal region and/or the coccyx region of the wearer's body, thereby supporting and holding the article 10 against the body of the wearer during use. The body adhesive 44 can overlie a portion of the first area 11 or optionally can overlie the entire first area 11 of the shell 14. Generally, the body adhesive 44 will be present on at least an outer portion or near the longitudinal edges 20A,20B of the article 10. The body adhesive 44 may also be placed in a pattern on the first area 11, such as shown in FIG. 14. The body adhesive 44 can be applied to the first area 11 of the shell 14 using any known process including, but not limited to, inkjet printing, screen printing or extruding the body adhesive 44 from one or more nozzles, slot coating and the like, and combinations thereof.

Generally, any pressure sensitive adhesive known to those skilled in the art may be used, although preferably the pressure sensitive adhesive is not a known irritant to human skin and preferably the adhesive is not so aggressive that it causes pain to the wearer when the article 10 is removed from the skin and/or hair. It is also desirable that the adhesive 44 is selected such that the adhesive does not leave a substantial amount of an adhesive residue on the surface of the skin of the wearer, when the article 10 is removed by the wearer after use. Particularly suitable pressure sensitive adhesive materials are disclosed in commonly assigned U.S. Pat. No. 6,213,993 to Zacharias et al. and U.S. Pat. No. 6,620,143 to Zacharias et al., which are incorporated herein by reference in a manner that is consistent herewith. Other suitable adhesives are disclosed in U.S. Pat. No. 5,618,281 to Batrabet et al., which is incorporated herein by reference in a manner that is consistent herewith. Other known body adhesives, such as those described in U.S. Pat. No. 6,316,524 to Corzani et al., which is incorporated by reference in a manner that is consistent herewith, may also be used. Additional examples of suitable pressure sensitive adhesives include hydrogels, hydrocolloids, acrylic based adhesives, and rubber based adhesives, such as KRATON based adhesives.

Referring to FIG. 15, the shell 14 consists of shell material 26, and body attachment means (or fastening means) 31. In some aspects, the body fastening means 31 is an adhesive transfer layer (ATL) having a carrier sheet 42, body adhesive 44 and release sheet 48. In some desirable aspects, the ATL 31 is applied to the body facing side 15 of the shell material 26. In some aspects, the body adhesive 44 is covered with release sheet 48.

In some aspects of the present invention, the body adhesive 44 may be placed on the entire first area 11, just outside of the absorbent structure 21. In other aspects of the present invention, as is shown in FIG. 15, the body adhesive 44 may be placed along the outer portions of the first area 11 near the distal ends 20A, 20B of the shell 14. In some aspects, the body adhesive 44 may also be placed on the absorbent structure 21. Generally, however, the body adhesive 44 is confined to being placed on the first area 11 of the shell 14, since placing the body adhesive on an area of the absorbent structure 21 which contacts the female genitalia such as the labia majora may cause discomfort to the wearer of the article.

In some aspects, the body adhesive 44 may be applied in a pattern of small discrete dots so as to leave numerous areas free from adhesive. Alternatively, the body adhesive may be applied as a continuous bead, or may be applied as a series of semi-continuous beads, such as shown in FIG. 14. Other suitable adhesive patterns may be selected for applying the body adhesive 44 to the body-contacting first area 11 of the article 10 without departing from the scope of the invention. For example, adhesive patterns can be circular, oval, swirls, various linear or non-linear arrays of adhesive longitudinally, and/or transversely, and/or any angle therebetween, and reticulated webs having unobstructed interstices between the adhesive fibers or combinations thereof. In addition, the adhesive patterns may be open or closed. The amount of adhesive is dependent upon the particular adhesive and various properties of the article, such as size, shape, weight, and the like. In some aspects, the weights of adhesives are limited to less than about 800 g/m$^2$, and generally less than about 400 g/m$^2$. Generally, the weight of the adhesive is at least 20 g/m$^2$. For example, the adhesive can be applied in an amount of about 100 to about 400 g/m$^2$. The limitations on the basis weight of the adhesive are a factor to provide the correct adhesive characteristics for applying directly to the wearer's vulva region and optionally the pubic, perinea, gluteal and/or coccyx regions of the wearer's body. If the basis weight is too high, the article will have a sticky feeling or otherwise uncomfortable feeling. If the basis weight of the adhesive is too low, there may be insufficient adhesion to the body of the wearer.

Generally, the body adhesive 44 is applied in a manner which is symmetrical about the longitudinally extending centerline A-A (e.g., FIG. 1) which bisects the article 10 and divides the article 10 into substantially equal portions. This symmetrical pattern provides the wearer a balanced feel when wearing the article 10. The symmetrical pattern also reduces the perception of any associated discomfort when the article 10 is removed from the body.

In some aspects, as is shown in FIG. 15, an optional peel sheet (i.e., release sheet) 48 may be used to prevent the body adhesive 44 from becoming contaminated, thus losing its ability to stick to the body of a wearer and/or prematurely adhering to an unintended surface. Suitable materials for use as a peel strip 48 are well known in the art and are commercially available. Examples of suitable peel sheets include, but are not limited to, a silicone coated Kraft paper, a silicone coated film, and the like. Other release coatings besides silicone include coatings containing polytetrafluoroethylene.

The release sheet 48 may extend beyond one or both of the ends and/or sides of the shell 14. Alternatively, the release sheet 48 may be sized to only cover the body adhesive on the first area 11 of the shell 14, as is shown in FIG. 15. In yet another aspect of the present invention, the release sheet 48 may extend beyond the adhesive 44 at one or more locations, such as one of the ends or one of the sides of the shell 14 by providing the release sheet 48 with a tab (not shown) for the wearer to grasp to remove the release sheet 48 from the article 10 and the body adhesive 44 on the article. When the release sheet 48 extends beyond the adhesive 44, it may be easier for the wearer to remove the release sheet 48 to place the article 10 for use.

Alternatively, the release sheet 48 may be provided with a pressure sensitive adhesive to hold the release sheet 48 in place when the article is devoid of an adhesive for body attachment (e.g., an alternative body attachment means). In this configuration, the release sheet serves to protect the first side 15 of the shell 14 and optionally the absorbent structure 21 from dirt and damage prior to use.

In some aspects, the optional release sheet 48 is not desirable. For example, the article may be rolled, folded onto itself or stacked upon adjacent articles. If rolled, the body adhesive 44 will generally contact the second side 17 of the shell 14. The body adhesive 44 should releasably stick to one second side of the shell 14 by readily releasing when unrolled by the wearer. In addition, it is desirable that the body adhesive 44 not leave a residue on the second side 17 of the shell 14. This should similarly occur when the articles 10 are stacked upon each other such that the body adhesive 44 of one article will attach or leave a residue on the second side 17 of the shell 14 of a second article. In another aspect, the article 10 may be folded longitudinally along the lateral axis 2 such that the body adhesive 44 in one area comes into contact with a surface in another area of the article. In cases of this aspect where the body adhesive of one area comes into contact with the body adhesive of another area, the body adhesive should be selected such that the body adhesive will release from the other body adhesive when manipulated by a wearer.

The dimensions and shape of the shell 14 should be such that it is appropriately sized for its intended use. The same is true for the size and shape of the absorbent structure 21. Generally, the size and shape of the absorbent structure 21, when present, will dictate the size and/or shape of the shell 14. The shape of the shell 14 is selected so that the article 10 will have a comfortable feeling for the wearer, thereby providing protection against leaks and preventing the article from becoming detached from the body of the wearer during wearing. In some aspects, the shell 14 may optionally be curved to better fit the body of a wearer. In some aspects, the shell 14 also generally gives the article 10 its overall size and shape in the longitudinal-1, lateral-2 and/or z-directions. That is, the shell 14 can be generally longer and/or wider than the absorbent structure 21, and may optionally have a 3-dimensional shape as well. For example, the shell 14 can be wider in the lateral direction 2 than the absorbent structure 21, and/or the shell can be longer in the longitudinal direction 1 than the absorbent structure 21. However, in some aspects, it is also possible for the absorbent structure 21 to be the same or longer and/or the same or wider than the shell 14.

When the article is intended for use as a pantiliner, a sanitary napkin, a maxi-pad or a feminine incontinence article, the shell 14 can be wider and longer than the absorbent structure 21 attached to the second area 12 of the shell 14. For example, the absorbent structure 21 can be at least as wide and as long as the labia majora of the wearer. As a result, to fit most women, the absorbent structure is longer in the longitudinal direction than it is wide in the lateral direction of the absorbent structure. Generally, for most women, the labia majora are generally between about 40 mm and about 70 mm in width and between about 80 mm and 150 mm in length. Ideally, the absorbent structure 21 should be wider than the labia majora and slightly longer that the labia minora and slightly longer than or equal to the labia majora. Generally, the absorbent structure 21 should be between about 40 mm and 90 mm in width in the lateral direction and between about 95 mm and about 150 mm in length in the longitudinal direction. The shape of the absorbent structure 21 will generally tend to be oblong and may be an oval, a rectangle, teardrop shaped, hourglass shaped or racetrack shaped, for example. As can be seen in FIG. 10, in some aspects, the absorbent structure 21 has a generally elliptical/hourglass shape to match the size and shape of the vaginal area of most women.

Generally, the shape of the shell 14 may vary. For example, in some aspects, the shell may have a generally oval shape. In other aspects, the shell may have a generally hourglass-like shape. By generally hourglass shape, it is meant a shape in which the sides of the shell converge towards one another at a point along the longitudinal axis of the shell to form a narrowest portion of the article. Generally, the hourglass-like shape provides a cut-out for the wearer's legs. By having an hourglass-like shape, the shell 14 will preferably not be attached to the legs of a wearer during use. This can provide additional comfort to the wearer of the article 10. The shape of the shell 14 can generally be any operative shape, or combination of shapes, and should be selected such that the article 10 will be comfortable to wear, while providing very effective leakage protection to the wearer. The shell 14 and the absorbent structure 21 should preferably be capable of adapting to the curvature of a wearer's body during use. In one particular aspect, as seen in FIG. 1, the shell 14 has a relative short and wide hourglass-like portion with a relatively long and narrow extension which ends in a bulbous portion. Other operative shapes not specifically shown are also suitable.

Figure 16:
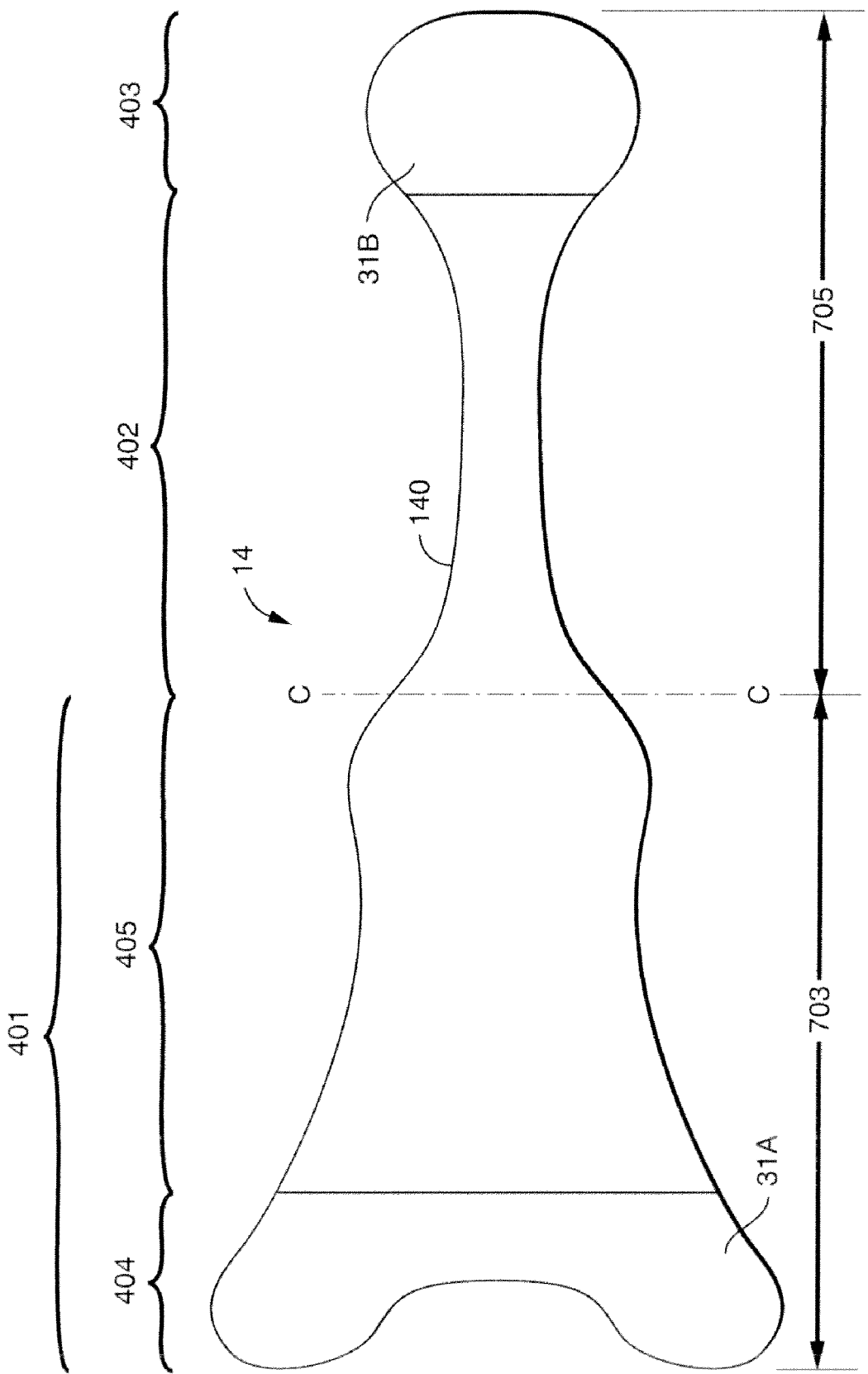
FIG. 16 is a top view of one aspect of a shell of the present invention.

FIG. 16 illustrates a shell 14 that has a generally fiddle shape. This fiddle shape is divided into three sections, body section 401, neck section 402, and head section 403. The body section 401 of the shell 14 consists of body adhering section 404 where anterior body adhering means 31A is located, and in the illustrated embodiment, absorbent article adhering section 405. With additional reference to FIG. 10, the anterior half 103 of the absorbent structure 21 is attached to the shell 14 in section 405. For reference purposes only, as illustrated in FIG. 16, line C-C divides the shell 14 transversely (2) at the longitudinally extending (1) midpoint into substantially equal portions Body section 401 occupies the anterior half 703 of the shell 14. Neck section 402 is located between the lateral center line C-C and the head section 403. The neck section 402 of the shell 14 is narrower than the rest of the chassis so that it will operatively fit within the gluteal groove of the wearer. The posterior body adhering means 31B is located in the head section 403 of shell 14. In some particular aspects, as illustrated in FIG. 16, the shell 14 has the following dimensional relationships:

The lateral direction 2 width of section 404 at its greatest extent is greater than or equal to lateral direction 2 width of sections 405, 402, and 403 at their greatest extent.

The area of the anterior half 703 of the shell 14 is greater than the area of the posterior half 705 of the shell 14.

The area of section 405 is greater than area of section 402.

The area of section 404 is greater than area of section 403.

The longitudinal direction 1 (length) of section 405 is greater than the longitudinal direction 1 (length) of section 404.

The longitudinal direction 1 (length) of section 402 is greater than the longitudinal direction 1 (length) of section 403.

The transition between section 402 and sections 403 and 405 along the peripheral edge 140 is primarily non-linear and has a concave shape.

In some aspects when the article is used as a feminine care article, to obtain an effective attachment of the article to the wearer, generally the width of the shell 14 should be at least 10 mm on either side of the labia majora. Generally, the portion of the shell 14 of the article 10 that will be located in the vulva region will have a width in the lateral direction 2 of about 50 mm up to 200 mm or more, such as about 60 mm to about 120 mm at its narrowest lateral point. With respect to FIG. 16, the above width dimensions would be suitable for section 405 of the illustrated embodiment. This will allow the shell 14 to have an anterior region 7 that can provide effective body attachment above the labia majora, and a posterior region 9 that can effectively fit into the gluteal groove of the wearer. For aspects such as FIG. 16 which have an extension of the shell 14, such as to operatively fit into the gluteal groove of the wearer, section 402 can have a width in the lateral direction 2 at its narrowest point of about 5 mm up to 70 mm or more, such as about 10 mm to about 60 mm, and section 403 can have a width in the lateral direction 2 at its widest point of about 10 mm up to about 160 mm or more, such as about 30 mm to about 80 mm to provide improved benefits.

The article also has a length dimension. Generally, the portion of the shell 14 of the article 10 that will be located in the vulva region will have a length in the longitudinal direction 1 of about 120 mm up to 300 mm or more, such as about 150 mm to about 200 mm at its narrowest longitudinal point. With respect to FIG. 16, the above dimensions would be suitable for section 405 of the illustrated embodiment. This will allow the shell 14 to have a anterior region 7 that can provide effective body attachment above the labia majora, and a posterior region 9 that can effectively fit into the gluteal groove of the wearer. For aspects such as FIG. 16 which have an anterior attachment means and an extension of the shell 14, such as to operatively fit into the gluteal groove of the wearer, the entire length of the article, which in most aspects is substantially defined by the length of the shell 14, can have a length in the longitudinal direction 1 of about 250 mm up to 400 mm or more, such as about 300 mm to about 385 mm, or about 315 mm to about 370 mm to provide improved benefits.

By providing specific portions for attachment to specific areas of the body of the wearer, the article may be configured to better fit the body of the wearer. In desirable aspects, the anterior region 7 of the article, such as shown in FIG. 3, will be the portion of the article between the absorbent structure 21 and the first end 20A of the article 10. The posterior region 9 of the article 10 in the illustrated embodiment will be the portion of the article between the absorbent structure 21 and the second end 20B of the article 10. In the illustrated embodiment, the posterior region 9 will be designed to be placed within the gluteal groove and to or through the coccyx area of the wearer. In desirable aspects, the anterior region 7 is designed to be placed in the pubic area above the vulva region of a female wearer. The central region 8 of the article 10 is designed to cover the vagina area of the wearer and the skin area surrounding the lateral sides of the labia majora, when the article is used as a pantiliner, sanitary napkin or an incontinence article.

In general, the article 10 is applied to the user when the user is in a somewhat upright position, although this need not be the case. In this particular aspect, the user applies some initial force to achieve the desired snugness of fit. In use, the user can typically bend approximately twenty degrees in the backward direction and greater than ninety degrees in the forward direction beyond the application angle. When bending forward beyond the application angle, the front of the body where the product is applied compresses and the back of the body where the product is applied expands. In some desirable aspects, the posterior half 705 of the shell 14 will exhibit greater strain than the anterior half 703 of the shell 14 when stress is applied to the entire article 10.

One important factor that has been discovered relative to body attachment is the minimal acceptable shear force. It has been found that many users, when applying the shell 14, pull the product close to the knee point to snug the product to the body. Accordingly, in some desirable aspects, the minimal shear strength should be greater than the knee point of the shell 14, such as illustrated graphically in FIG. 17. In particular, FIG. 17 shows that the minimum shear force of the body attachment is desirably greater than the force at the "knee" of the curve 801 in order to minimize unintended detachment of the article when in use. In addition, extending an elasticized member past the knee point provides a cue that the member is cinching and becoming secure. This rapid change in curve slope is an intuitive cue to the user that the article is secure.

It has been found that increasing the stiffness and/or reducing the stretch properties of the body attachment means/shell composite (31/14) can improve comfort and/or ease of removal for the user at the time of removal. This may be accomplished by using specific materials in the body attachment section of the shell which increase the stiffness and/or reduce the stretch properties of that portion of the shell, or may be the result of the attachment means itself when applied to the shell. For example, due to the carrier sheet 42 and adhesive 44 of an ATL if present, the body attachment means 31/shell 14 composite may have a higher stiffness than the remainder of the shell, and thus would be easier and more comfortable to remove from the wearer's body. Without being held to one particular theory, it is believed that a higher stiffness and/or lower stretch of the body attachment means 31/shell 14 composite relative to the remainder of the article 10 changes the peel angle at removal, which has the affect of spreading the removal force over a wider area when the shell is removed. For example, if a lower peel angle is at least partially responsible for improved user comfort, then having a composite stiffness greater than that of human skin would be desirable.

Figure 11:
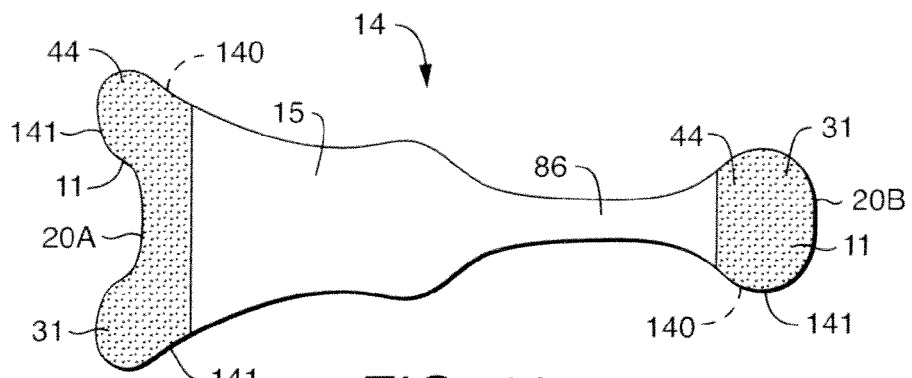
FIG. 11 is a top view of one aspect of an absorbent article of the present invention illustrating a body attachment means.
Figure 12:
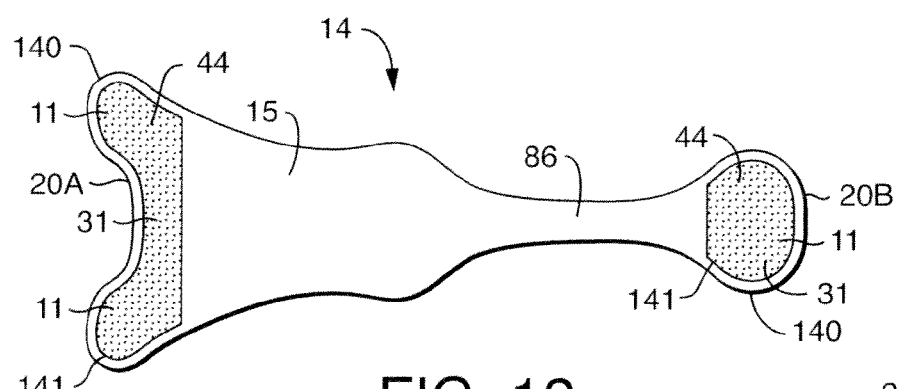
FIG. 12 is a top view of one aspect of an absorbent article of the present invention illustrating a body attachment means.
Figure 13:
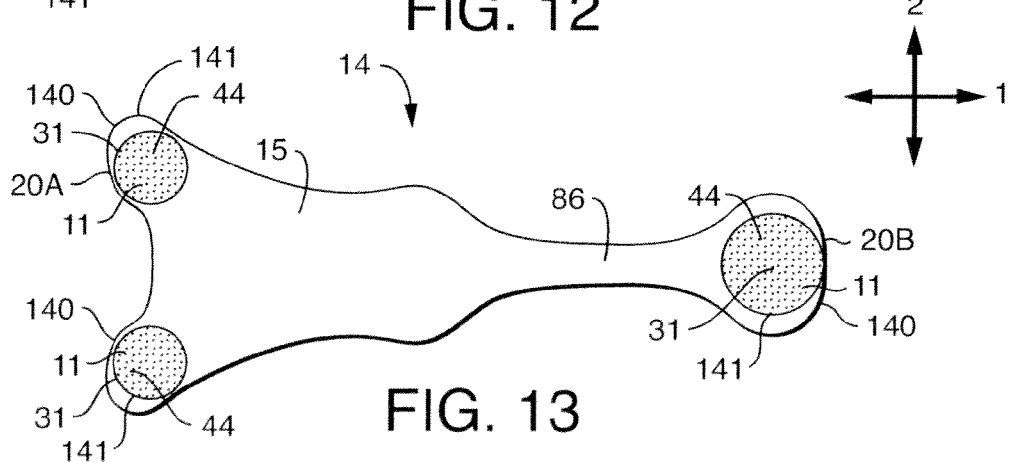
FIG. 13 is a top view of one aspect of an absorbent article of the present invention illustrating a body attachment means.
Figure 14:
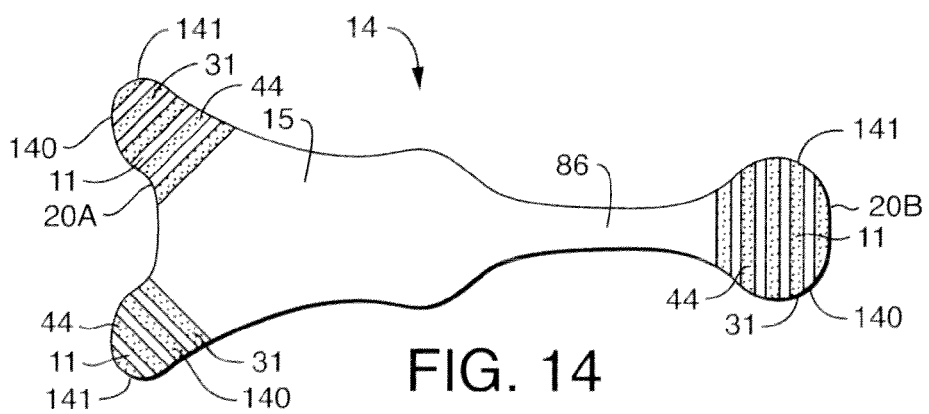
FIG. 14 is a top view of one aspect of an absorbent article of the present invention illustrating a body attachment means.

In some aspects, as illustrated in FIGS. 11-14, the shell 14 includes attachment means 31 applied to first side 15. In some aspects, the attachment means 31 are coextensive with at least a portion of the shell peripheral edge 140 as shown in FIGS. 11 and 14. In other aspects, there can be a gap between the shell peripheral edge 140 and the attachment means 31 peripheral edge 141 as shown in FIGS. 12 and 13. In a particular aspect, the attachment means 31, or components of the attachment means 31, such as an optional carrier sheet 42 (FIG. 15), can be elastic or extensible in at least one direction to enhance the extension of the shell 14. In other aspects, the body adhesive 44 can be applied to the shell material 26 or carrier sheet 42 in discrete segments as shown in FIGS. 13 and 14.

Figure 18:
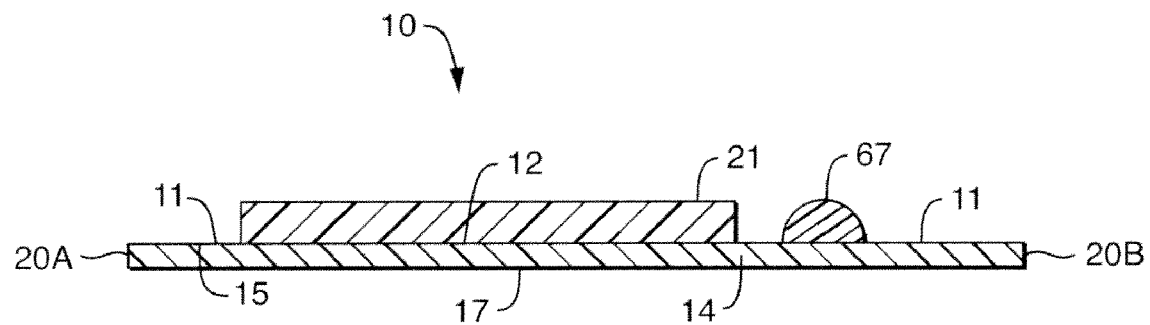
FIG. 18 is a longitudinal cross section view of one aspect of an absorbent article taken along line A-A of FIG. 1 and having a protrusion.

To obtain an effective attachment to the body of the wearer, the shell 14 can be configured to be anatomically correct for a wearer. As referenced earlier, the shape of the article 10 is such that it will correctly and securely fit in the vulva region of a wearer. Additional features may also be included to ensure an anatomically correct shape. For example, in the posterior region 9 of the article 10 of FIGS. 1 and 18, more particularly, the posterior region 9 of the shell on the first side 15, the shell 14 may be imparted with a three-dimensional protrusion 67. The protrusion 67 acts to fit comfortably in the perinea region of the wearer. The protrusion 67 may be formed from the shell material 26 or may be formed from the body adhesive 44, or some other material as desired. By providing the three-dimensional protrusion 67, the article can effectively fit to the typical body shape of the female wearer, thereby preventing leaks from the posterior portion of the article. The protrusion 67 may also serve as a guide to the wearer in placement of the article 10 on the body prior to use.

Figure 19:
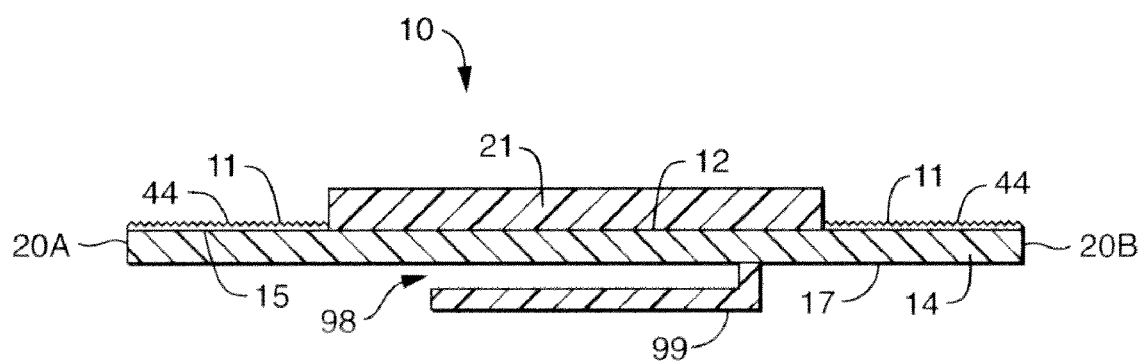
FIG. 19 is a longitudinal cross section view of one aspect of an absorbent article taken along line A-A of FIG. 1 and having a positioning aid.

The article of the present invention may have other features which aid the wearer to place and remove the article from the body. As is shown in FIG. 19, the second side 12 of the shell 14 may be provided with article positioning aids such as a finger pocket 99 and/or finger grooves in the shell material. In the illustrated embodiment, the finger pocket 99 has an opening 98 towards the anterior edge 20A of the article 10. The pocket 99 gives the wearer a location to place her fingers during placement of the article 10 onto the wearer's body. The pocket 99 may be an opening wide enough for the wearer to place one or more fingers in the pocket. Alternatively, the article can comprise two or more openings which allow the wearer to place only one finger in each opening. Other similar article positioning aids may be used to help guide a wearer to properly position the article for use. For example, grooves may be placed in the second side 17 of the shell 14 opposite the absorbent structure 21. This can allow the wearer to feel the location of the absorbent structure 21 relative to the vulva region during application of the article 10 to the vulva region of the body. The pocket 99 can also assist the wearer in removing the article from their body.

In some aspects, the article 10 can optionally be provided with an article removal aid which provides the wearer with an easy way to grasp and remove the article when attached to the body. One particular article removal aid is shown in FIG. 15 including a tab 92 located on the anterior edge 20A of the shell 14 which is not adhered to the body or is devoid of adhesive. Alternatively, other article removal aids can be utilized, such as having an area of the anterior edge 20A or posterior edge 20B region being devoid of the body attaching adhesive 44. Other types of article removal aids which may be present include loops, pull strings, and the like. The article removal aid allows the wearer to effectively begin the process of gently removing the article from the body of the wearer, without the need of having to find a portion of the shell which may not be completely attached.

Other features or additives may be incorporated into the article of the present invention. For example, the article may contain an odor control agent, a fragrance, a skin wellness agent and other similar additives used in currently available disposable absorbent articles. Any odor control agent, fragrance or wellness agent known to those skilled in the art can be used in the article of the present invention. The odor control agent, fragrance or wellness agent may be added in various components of the article, including the shell 14, the absorbent structure 21 or the body adhesive 44, for example.

Generally, with reference to FIG. 15, to apply the article 10 to the body of a wearer, the release sheet(s) 48, if present, protecting the body adhesive 44 and/or absorbent structure 21 is removed from the first surface 15 of the shell 14. Next, the wearer positions the shell 14, or absorbent structure 21, onto the portion of the body in which protection is desired. If positioning pockets or other article positioning aids are present on the article, the wearer may optionally use these article positioning aids to properly place the article for use. In the case of disposable feminine care absorbent articles, the absorbent structure 21 is positioned over the vagina area such that the absorbent structure will absorb body fluids. The wearer then checks to ensure that the first area 11 of the shell or the adhesive 44 is contacting the skin and/or hair around the vagina area. With respect to FIG. 1, the posterior region 9 of the article 10 is then positioned into the gluteal groove, and the attachment means adjacent the posterior edge 20B is attached to the coccyx area of the wearer's body.

If the article is intended to have an anterior region 7 and a posterior region 9, such as shown in FIG. 1, the wearer first identifies the anterior region and/or the posterior region of the article. To aid in identification of the anterior and posterior regions, indicia may optionally be located on the release sheet 48, shell 14 or absorbent structure 21 to indicate the anterior region 7 and/or posterior region 9 of the article 10. Indicia can be simply lettering or a picture to indicate the front or back of the article. Other examples include, color, wording, diagrams and the like, which would indicate to a wearer the anterior and posterior regions of the article. In some aspects, a set of instructions can also be included with the article which aids the wearer in determining proper placement and use. Once the anterior region and posterior region are identified by the wearer, the wearer places the article in the same manner described above.

In some aspects, the article can be positioned with the aid of the absorbent structure. More specifically, the absorbent structure, when sized and shaped to the approximate size of the labia majora, can serve to guide the placement of the absorbent structure over the labia majora. Once properly placed, pressure is applied by the wearer to the second surface of the shell which will allow the first surface of the shell to contact the skin and/or hair of the wearer, or to allow any adhesive applied to the first surface to be applied to the skin and/or hair of the wearer.

By having the article 10 attached to the body of a wearer, the article 10 will desirably move with the skin of the wearer. This results in an article that is comfortable to wear and which will be less likely to leak than conventional personal care articles. The article of the present invention advantageously has a very close to the body fit which can provide improved discretion and confidence for the wearer as compared to conventional personal care articles. In addition, because of the particular attachment configuration of the absorbent structure 21 to the shell 14 of the present invention, the article 10 provides a snug fit with minimal gaps for a wide range of consumers over the entire range of movement.

FIGS. 1, 9 and 20 illustrate one aspect of a body adhesive personal care article 10 of the present invention. The shell 14 has an anterior region 7, a central region 8, and an elongated posterior region 9 extending from the central region. The shell 14 also has a first side 15, which defines a body-facing surface, and a second side 17, which defines a garment-facing surface. The first side 15 of the shell 14 has first area 11 and a second area 12. In the illustrated embodiment, the first side 15 of the shell 14 has a body adhesive 44 on at least a portion thereof for adhering the article 10 directly to the wearer's skin and/or hair, and particularly, to a female wearer's skin and/or hair surrounding her vulva region for the illustrated article. The body adhesive 44 contacts the skin and/or hair in the vulva region and/or the pubic region and/or the perinea region, for example, of the wearer's body, thereby supporting and holding the shell 14 and the absorbent structure 21 against the body of the wearer during use.

In the illustrated embodiment, the shell 14 contains adhesive 44 in at least a portion of the anterior region 7 and in only a portion of the posterior region 9. It is understood that the entire exposed area (i.e., the area not covered by the absorbent structure 21, that is, the first area 11) can have adhesive 44 thereon without departing from the scope of this invention. A release sheet 48 may be used to prevent the body adhesive 44 from becoming contaminated, thus losing its ability to stick to the body of the wearer and/or prematurely adhering to an unintended surface. The absorbent structure 21 is suitably secured to the first side 15 of the shell 14 at the central region 8 and is sized and located relative to the shell such that the shell extends longitudinally outward beyond the periphery 121 of the absorbent structure. In some aspects, the article can include an absorbent material coated onto and/or integrated into the shell 14.

The anterior region 7 of the article 10 is suitably contoured along the width of the shell 14 to accommodate the lower abdomen region of the wearer. In the illustrated embodiment of FIGS. 1, 9 and 20, for example, the longitudinal 1 extent (e.g., length) of the shell 14 relative to the transverse axis 2 of the article is non-uniform across the width of the shell at the anterior region 7 of the article 10. In this particular aspect of the illustrated embodiment, the longitudinal edge of the shell 14 (i.e., at anterior edge 20A of article 10 in the illustrated embodiment) is generally U-shaped as it extends across the width of the shell at its longitudinal edge 20A. It is understood, however, that the contour of the longitudinal edge 20A of the shell 14 may be inwardly arcuate, V-shaped, transversely straight, outwardly arcuate or other suitable shape without departing from the scope of this invention.

In this particular aspect of FIGS. 1, 9 and 20, the sides of the article 10 and more particularly the longitudinal side edges 19 of the shell 14 are generally inwardly arcuate along at least a portion of the length of the article 14. Alternatively, the sides 19 may be inwardly arcuate along substantially the entire length of the article. It is also understood that the sides 19 defining the leg cutouts may be V-shaped, U-shaped, outwardly arcuate or other suitable shape, or it may be uniform (e.g., straight or longitudinal) along substantially the entire length of the article 10.

In this particular aspect of FIGS. 1, 9 and 20, the contoured longitudinal end edge of the shell 14 (e.g., anterior edge 20A of the article 10) together with the contoured longitudinal side edges of the shell 19 where these side edges generally intersect the longitudinal edge of the shell, define a pair of transversely spaced tabs 520. Each of the tabs 520 suitably has body adhesive 44 on the body-facing surface (e.g., first side 15) for adhering the tabs directly to the wearer and more suitably to the abdomen region of the wearer. In some aspects, the tabs 520 are sized to extend to a region of the wearer that has little or no pubic hair to facilitate adherence to the wearer's skin, although it need not be. For example, in some aspects, it is desirable to provide a shape that attaches to the hairs in the region.

The elongated portion 532 of the shell 14 includes a tab 532' for generally aligning with the coccyx of the wearer. The tab 532' has adhesive thereon for adhering the shell 14 to the body of the wearer. The tab 532' of the illustrated embodiment is generally bulbous in shape but it is understood that the tab could have other shapes without departing from the scope of the invention. In some aspects, the elongated portion 532 can additionally or alternatively rely on friction within the gluteal groove to provide additional attachment of the article to the body. Accordingly, in some aspects of the illustrated embodiment, the elongated portion 532 comprises no body adhesive.

Other benefits of the article 10 of the present invention may also be provided. For example, when the first side 15 of the shell 14 has an adhesive applied thereto, upon removal of the article 10 after use, the wearer may fold the first side 15 of the shell 14 onto itself to dispose of the used article. An effective seal may be formed around the perimeter of the shell, thereby effectively encapsulating bodily fluids within a closure. As a result, any odors associated with the fluids will be contained within the shell material. Another advantage of the article of the present invention is a tampon backup article. For example, the article can be effective in hiding the withdraw string of a tampon, while providing additional leakage protection.

The article described above can be an individual article or may be part of a personal care system, offering the wearer a wide variety of options to fill the needs of the wearer. For example, the shell 14 can be provided to wearers in a variety of shapes or sizes to allow wearers to select the appropriate shape or size for their given body shape or degree of fluid flow. Likewise, the body adhesive 44 may be provided in a variety of adhesive strengths to match the adhesive strength needed or desired by the wearer. By providing a variety of adhesive or other attachment means, a wearer could select shells to match body type, body condition and other various factors that may vary from one wearer to another. Similarly, the absorbent structure 21 could be provided in various absorbent capacities so that the wearer could select the appropriate absorbency to match the wearer's needs.

The personal care system may be provided to wearers in a variety of packaging arrangements. In one packaging arrangement, a plurality of shells 14 having different properties may be provided in separate packages or could be provided in a single package. It is generally a better packaging arrangement if shells having similar properties, shapes or sizes are provided in a single package. That is, in a given package, the wearer is provided with a plurality of shells all having the same shape, size, and properties, such as similar body attachment properties. Regarding the absorbent structures 21, the absorbent structures could be provided to the wearer in packages sorted by absorbent capacity or various absorbent capacity structures could be provided in a single package. By having all absorbent structures in a single package with a single absorbent capacity, a wearer is able to select the correct absorbent capacity for their typical needs. However, by providing different absorbent capacity absorbent structures in a single package, the wearer will be provided with the ability to select the absorbent structure with the appropriate absorbent capacity for a given situation, without the need to purchase multiple packages of absorbent structures.

It will be appreciated that details of the foregoing examples, given for purposes of illustration, are not to be construed as limiting the scope of this invention. Although only a few exemplary embodiments of this invention have been described in detail above, those skilled in the art will readily appreciate that many modifications are possible in the examples without materially departing from the novel teachings and advantages of this invention. For example, features described in relation to one example may be incorporated into any other example of the invention.

Accordingly, all such modifications are intended to be included within the scope of this invention, which is defined in the following claims and all equivalents thereto. Further, it is recognized that many embodiments may be conceived that do not achieve all of the advantages of some embodiments, particularly of the desirable embodiments, yet the absence of a particular advantage shall not be construed to necessarily mean that such an embodiment is outside the scope of the present invention. As various changes could be made in the above constructions without departing from the scope of the invention, it is intended that all matter contained in the above description shall be interpreted as illustrative and not in a limiting sense.

The invention claimed is:

1. A disposable personal care article comprising:
   a shell having a unitary structure for disposition adjacent a wearer's vulva region;
   wherein the shell has a first side and a second side, the first side having a first area and a second area, the first area including body adhesive properties;
   wherein the first area of the shell contacts to the wearer's skin and/or hair surrounding the vulva region;
   wherein at least a portion of the first area comprises a body attachment means for adhering the shell directly to the skin and/or hair of the wearer; and
   wherein the shell has an anterior half and a posterior half where the posterior half exhibits a higher % Extension relative to the anterior half when a stretching force of 454 grams is applied, as measured by the % Strain Differential Test; and
   an absorbent structure present in the second area of the shell, wherein the first area is longitudinally separated from the second area.

2. The disposable personal care article of claim 1, wherein the shell comprises a woven web, nonwoven web, a gel, a film, a sheet of a polymeric material, a foam, or a laminate.

3. The disposable personal care article of claim 1, wherein the shell comprises a silicone material.

4. The disposable personal care article of claim 1, wherein the first area of the shell has an anterior half and a posterior half, wherein at least a portion of the anterior half of the shell and at least a portion of the posterior half of the shell each comprise body adhesive properties, wherein the body adhesive properties provide a means to attach the personal care article directly to the wearer's body.

5. The disposable personal care article according to claim 1, wherein the shell has an anterior half and a posterior half, wherein at least a portion of the posterior half is adapted to attach to the body of a wearer between the vulva region and the coccyx of the body of the wearer and at least a portion of the anterior half is adapted to attach to the pubic area above the vulva region of the wearer.

6. The disposable personal care article of claim 1, wherein the shell is breathable.

7. The disposable personal care article of claim 1, wherein the shell comprises material that is selected from extensible or elastically extensible materials, or combinations thereof.

8. The disposable personal care article according to claim 1, wherein at least a portion of the first area of the shell further comprises at least one of a release sheet, a carrier sheet, or an adhesive transfer layer.

9. The disposable personal care article according to claim 1, wherein the body attachment means and shell form a body attachment means/shell composite having a higher stiffness and/or a lower stretch than the remainder of the shell.

10. The disposable personal care article of claim 1, wherein the anterior absorbent structure attachment is a permanent attachment means, and the posterior absorbent structure attachment is a refastenable attachment means.

11. The disposable personal care article of claim 1, wherein the body attachment means is an adhesive.

12. The disposable personal care article of claim 1, the absorbent structure configured for disposition adjacent a wearer's vulva region;
   wherein the absorbent structure has an anterior half and a posterior half;
   wherein the absorbent structure is attached to the shell via an absorbent structure attachment means in the anterior half and in the posterior half of the absorbent structure; and wherein the absorbent structure attachment means is selected from an anterior point bond, a posterior point bond or a U-shaped attachment, or combinations thereof.

13. A disposable personal care article comprising:

a shell having a unitary structure for disposition adjacent a wearer's vulva region, wherein the shell has a first side and a second side, the first side having a first area and a second area, wherein the first area of the shell contacts to the wearer's skin and/or hair surrounding the vulva region, wherein at least a portion of the first area comprises a body attachment means for adhering the shell directly to the skin and/or hair of the wearer, and wherein the shell has an anterior half and a posterior half where the posterior half exhibits a higher % Extension relative to the anterior half when a stretching force of 454 grams is applied, as measured by the % Strain Differential Test;

an absorbent structure configured for disposition adjacent a wearer's vulva region, wherein the absorbent structure has an anterior half and a posterior half, wherein the absorbent structure is present in the second area of the shell, wherein the absorbent structure is attached to the shell via an absorbent structure attachment means in the anterior half and in the posterior half of the absorbent structure, and wherein the absorbent structure attachment means is selected from an anterior point bond, a posterior point bond or a U-shaped attachment, or combinations thereof; and an anterior point bond and a posterior point bond, wherein the anterior point bond has a coverage area of about 5 mm$^2$-about 200 mm$^2$ and the posterior point bond has a coverage area of about 5 mm$^2$-about 200 mm$^2$, wherein the bonds are longitudinally aligned along the longitudinal centerline of the personal care article and wherein the anterior point bond and the posterior point bond are separated by a distance of at least about 5 mm.

14. The disposable personal care article of claim 12, wherein the absorbent structure is at least partially free-floating.

15. The disposable personal care article according to claim 12, wherein the absorbent structure further comprises at least one of a topsheet, a backsheet, a surge layer or a transfer layer.

16. The disposable personal care article according to claim 12, further comprising at least one of an absorbent structure positioning aid, an article positioning aid, or an article removal aid.

17. The disposable personal care article according to claim 12, wherein the shell further comprises an absorbent material.

18. The disposable personal care article according to claim 12, wherein the absorbent structure attachment means is present as an anterior absorbent structure attachment means and a posterior absorbent structure attachment means, wherein the anterior absorbent structure attachment means is a permanent attachment and the posterior absorbent structure attachment means is a refastenable attachment.

19. The disposable personal care article of claim 1, wherein the shell has a lower coefficient of friction than the adjacent surface of a garment with which the shell comes in contact with.

20. The disposable personal care article according to claim 1, wherein the personal care article is selected from a pantiliner, a sanitary napkin, a maxi-pad or an incontinence article.

* * * * *